United States Patent
You et al.

(10) Patent No.: US 11,649,447 B2
(45) Date of Patent: May 16, 2023

(54) COMPOSITIONS, SYSTEMS, AND METHODS FOR THE PRODUCTION OF BIOMOLECULES

(71) Applicant: Duke University, Durham, NC (US)

(72) Inventors: Lingchong You, Durham, NC (US); Anna Lee, Durham, NC (US); Zhuojun Dai, Durham, NC (US)

(73) Assignee: Duke University, Durham, NC (US)

( * ) Notice: Subject to any disclaimer, the term of this patent is extended or adjusted under 35 U.S.C. 154(b) by 455 days.

(21) Appl. No.: 16/621,615

(22) PCT Filed: Jun. 12, 2018

(86) PCT No.: PCT/US2018/037111
§ 371 (c)(1),
(2) Date: Dec. 11, 2019

(87) PCT Pub. No.: WO2018/231834
PCT Pub. Date: Dec. 20, 2018

(65) Prior Publication Data
US 2020/0109393 A1  Apr. 9, 2020

Related U.S. Application Data

(60) Provisional application No. 62/518,075, filed on Jun. 12, 2017.

(51) Int. Cl.
| C12N 11/04 | (2006.01) |
| C12M 1/12 | (2006.01) |
| C12N 15/70 | (2006.01) |
| C12N 15/81 | (2006.01) |
| C12P 21/02 | (2006.01) |

(52) U.S. Cl.
CPC ............. *C12N 11/04* (2013.01); *C12M 25/06* (2013.01); *C12N 15/70* (2013.01); *C12N 15/81* (2013.01); *C12P 21/02* (2013.01)

(58) Field of Classification Search
CPC ................................. C12N 11/04; C12N 15/70
See application file for complete search history.

(56) References Cited

U.S. PATENT DOCUMENTS

| 4,554,101 A | 11/1985 | Hopp |
| 4,801,529 A | 1/1989 | Perlman |
| 2009/0018195 A1 | 1/2009 | Balagadde et al. |
| 2009/0226984 A1 | 9/2009 | Nonaka et al. |
| 2011/0189743 A1 | 8/2011 | Yoshikuni et al. |
| 2014/0287489 A1 | 9/2014 | Lee et al. |
| 2015/0026840 A1 | 1/2015 | Kerfeld et al. |
| 2016/0015781 A1 | 1/2016 | Olschlager et al. |

FOREIGN PATENT DOCUMENTS

| WO | WO 2000/065030 | 11/2000 |
| WO | WO 2018/017845 | * 1/2018 |

OTHER PUBLICATIONS

Papi et al., "Encapsulated *Escherichia coli* in alginate beads capable of secreting a heterologous pectin lyase", Microbial Cell Factories, 2005, 4:35, pp. 1-8. doi:10.1186/1475-2859-4-35.*
International Search Report and Written Opinion for PCT/US18/37111. dated Sep. 11, 2018. 14 pages.
Bradley et al., Tools and Principles for Microbial Gene Circuit Engineering. J Mol Biol. Feb. 27, 2016;428(5 Pt B):862-88.
Kyte et al., A simple method for displaying the hydropathic character of a protein. J Mol Biol. May 5, 1982;157(1):105-32.
You et al., Programmed population control by cell-cell communication and regulated killing. Nature. Apr. 22, 2004;428(6985):868-71.
Balagaddé, et al., Long-term monitoring of bacteria undergoing programmed population control in a microchemostat. Science. Jul. 1, 2005;309(5731):137-40.
Carnes et al., Confinement-induced quorum sensing of individual *Staphylococcus aureus* bacteria. Nat Chem Biol. Jan. 2010;6(1):41-5.
Chang, Therapeutic applications of polymeric artificial cells. Nat Rev Drug Discov. Mar. 2005;4(3):221-35.
Dai et al., Microgel particles: The structure-property relationships and their biomedical applications. Journal of Polymer Science Part a-Polymer Chemistry 2013: 51, 2995-3003.
Din et al., Synchronized cycles of bacterial lysis for in vivo delivery. Nature. Aug. 4, 2016;536(7614):81-85.
Ebara et al., Smart Biomaterials. Springer, 2014. TOC only. 10 pages.
Ford et al., Synthetic biology expands chemical control of microorganisms. Curr Opin Chem Biol. Oct. 2015;28:20-8.
Ganji et al., Hydrogels in Controlled Drug Delivery Systems. Iranian Polymer Journal. 2009: 18, 63-88.
Ge et al., Purification of an elastin-like fusion protein by microfiltration. Biotechnol Bioeng. Oct. 20, 2006;95(3):424-32.
Gu et al., Glucose-responsive microgels integrated with enzyme nanocapsules for closed-loop insulin delivery. ACS Nano. Aug. 27, 2013;7(8):6758-66.
Hassouneh et al., Elastin-like polypeptides as a purification tag for recombinant proteins. Curr Protoc Protein Sci. Aug. 2010;Chapter 6:Unit6.11. 20 pages.
Hassouneh et al., Fusions of elastin-like polypeptides to pharmaceutical proteins. Methods Enzymol. 2012;502:215-37.
Hoffman, Hydrogels for biomedical applications. Adv Drug Deliv Rev. Jan. 17, 2002;54(1):3-12.

(Continued)

*Primary Examiner* — Suzanne M Noakes
(74) *Attorney, Agent, or Firm* — Peter J. Schlueter; Casimir Jones, S.C.

(57) ABSTRACT

The present disclosure relates to compositions, systems, and methods for the production of biomolecules using microorganisms. In particular, the present disclosure provides biomolecule production platforms that include genetically engineered microorganisms with genetic circuits functionally coupled to microcapsules formed from materials that are responsive to culture conditions. The biomolecule production platforms disclosed herein facilitate the efficient and robust production, purification, and/or analysis of any biomolecule-of-interest.

19 Claims, 27 Drawing Sheets

(56) References Cited

OTHER PUBLICATIONS

Huang et al., Coupling spatial segregation with synthetic circuits to control bacterial survival. Mol Syst Biol. Feb. 29, 2016;12(2):859.
Ihssen et al., Production of glycoprotein vaccines in *Escherichia coli*. Microb Cell Fact. Aug. 11, 2010 ;9:61. 13 pages.
Ionov, Hydrogel-based actuators: possibilities and limitations. Materials Today. 2014: 17, 494-503.
Khalil et al., Synthetic biology: applications come of age. Nat Rev Genet. May 2010;11(5):367-79.
Klouda et al., Thermoresponsive hydrogels in biomedical applications. Eur J Pharm Biopharm. Jan. 2008;68(1):34-45.
Kwon et al., High quality protein microarray using in situ protein purification. BMC Biotechnol. Aug. 23, 2009;9:72.
Lopez-Leon et al., Physicochemical characterization of chitosan nanoparticles: electrokinetic and stability behavior. J Colloid Interface Sci. Mar. 15, 2005;283(2):344-51.
Marguet et al., Oscillations by minimal bacterial suicide circuits reveal hidden facets of host-circuit physiology. PLoS One. Jul. 30, 2010;5(7):e11909. 11 pages.
Meyer et al., Purification of recombinant proteins by fusion with thermally-responsive polypeptides. Nat Biotechnol. Nov. 1999;17(11):1112-5.
Meyer et al., Quantification of the effects of chain length and concentration on the thermal behavior of elastin-like polypeptides. Biomacromolecules. May-Jun. 2004;5(3):846-51.
Naderi et al., Review paper: critical issues in tissue engineering: biomaterials, cell sources, angiogenesis, and drug delivery systems. J Biomater Appl. Nov. 2011;26(4):383-417.
Nguyen et al., Injectable biodegradable hydrogels. Macromol Biosci. Jun. 11, 2010;10(6):563-79.
Oh et al., The development of microgels/nanogels for drug delivery applications. Progress in Polymer Science 2008: 33, 448-477.
Osada et al., A polymer gel with electrically driven motility. Nature, 1992; 355, 242-244.
Pai et al., Optimal tuning of bacterial sensing potential. Mol Syst Biol. 2009;5:286. 11 pages.
Pardee et al., Portable, On-Demand Biomolecular Manufacturing. Cell. Sep. 22, 2016;167(1):248-259.e12.
Perez-Pinera et al., Synthetic biology and microbioreactor platforms for programmable production of biologies at the point-of-care. Nat Commun. Jul. 29, 2016;7:12211. 10 pages.
Santi et al., Biological nitrogen fixation in non-legume plants. Ann Bot. May 2013;111(5):743-67.
Slomovic et al., Synthetic biology devices for in vitro and in vivo diagnostics. Proc Natl Acad Sci USA. Nov. 24, 2015;112(47):14429-35.
Tanouchi et al., Programming stress-induced altruistic death in engineered bacteria. Mol Syst Biol. 2012;8:626.
Trongsatitkul et al., Temperature dependence of serum protein adsorption in PEGylated PNIPAm microgels. Colloids Surf B Biointerfaces. Mar. 1, 2013;103:244-52.
Vinogradov, Colloidal microgels in drug delivery applications. Curr Pharm Des. 2006;12(36):4703-12.
Bhatla, N. et al., "Light and hydrogen peroxide inhibit C. elegans feeding through gustatory receptor orthologs and pharyngeal neurons." Neuron 85.4 (2015): 804-818.
Edwards S.L. et al., "A novel molecular solution for ultraviolet light detection in Caenorhabditis elegans." PLoS biology 6.8 (2008): e198.
Huang, S. et al., "Dynamic control and quantification of bacterial population dynamics in droplets." Biomaterials 61 (2015): 239-245.
Yu, W. et al., "Study on membrane characteristics of alginate-chitosan microcapsule with cell growth." Journal of Membrane Science 377.1-2 (2011): 214-220.

\* cited by examiner

C

COMPOSITIONS, SYSTEMS, AND METHODS FOR THE PRODUCTION OF BIOMOLECULES

CROSS-REFERENCE TO RELATED APPLICATIONS

This application is a national phase application under 35 U.S.C. § 371 of PCT International Application No. PCT/US2018/037111, filed Jun. 12, 2018, which claims priority to U.S. Provisional Application No. 62/518,075, filed Jun. 12, 2017, each of which are hereby incorporated by reference in its entirety.

GOVERNMENT FUNDING

This invention was made with Government support under Federal Grant Nos. R 01 GM098642 and CBET-0953202 awarded by the NIH and NSF, respectively. The Federal Government has certain rights to the invention.

RELATED APPLICATIONS

This application claims priority to and the benefit of U.S. Provisional Patent Application No. 62/518,075 filed Jun. 12, 2017, which is incorporated herein by reference in its entirety for all purposes.

FIELD

The present disclosure provides compositions, systems, and methods relating to the production of biomolecules using microorganisms. In particular, the present disclosure provides biomolecule production platforms that include genetically engineered microorganisms with genetic circuits functionally coupled to microcapsules formed from materials that are responsive to culture conditions. The biomolecule production platforms disclosed herein facilitate the efficient and robust production, purification, and/or analysis of any biomolecule-of-interest.

BACKGROUND

Stimulus-sensitive biomaterials have found diverse applications including controlled drug release and injectable implants due to their phase transition capability. In parallel, engineered bacteria programmed with synthetic gene circuits have shown tremendous potential as "smart" sensing and actuating agents. To date, few efforts have been made to integrate these two aspects. Yet, the function of many natural systems emerges from the interplay between cells and their changing environment.

"Smart" hydrogels, or stimuli-responsive hydrogels, can undergo reversible volume phase transitions upon minute changes in physical (e.g., temperature, light) or chemical (e.g., pH, ions) environments. Due in part to their unique properties, smart hydrogels have been entailed for transducing chemical or physical energy into mechanical work as sensors; controlled release of the drug at proper condition for therapeutic drug delivery; and sol-gel transition in situ in tissue engineering. In parallel, the past two decades have seen enormous progress in synthetic biology, leading to engineering of cell-based systems for sensing and responding to diverse signals and also to their physical confinement. This allows the engineered systems not only to function as biosensors or biomarkers, but also be applied in targeted drug delivery and on-demand protein synthesis.

SUMMARY

Embodiments of the present disclosure include a system for biomolecule production. In accordance with these embodiments, the system includes a plurality of genetically engineered microorganisms comprising a genetic circuit and means for producing a biomolecule-of-interest, wherein the genetic circuit facilitates autonomous production of the biomolecule-of-interest; and an encapsulation material, wherein the encapsulation material is capable of forming microcapsules to contain the plurality of genetically engineered microorganisms, and wherein the microcapsules are functionally coupled to the genetic circuit.

In some embodiments, the plurality of genetically engineered organisms includes bacteria or yeast. In some embodiments, the plurality of genetically engineered organisms includes one or more strains of E. coli. In some embodiments, the one or more strains of E. coli include MC4100, MG1655, BL21, NISSLE1917, and any derivatives or variations thereof. In some embodiments, the genetic circuit includes a cell lysis module and a cell density sensing module. In some embodiments, the cell lysis module includes a gene encoding E protein from phage phiX174, and the cell density sensing module includes a mutated luxR gene and a ColE1 origin of replication lacking the Rom/Rop protein. In some embodiments, the biomolecule-of-interest is at least one of a peptide, a polypeptide, a protein, a nucleic acid, a polynucleic acid, a DNA molecule, a RNA molecule, or any derivatives or combinations thereof. In some embodiments, the biomolecule-of-interest is a polypeptide, and the means for producing the biomolecule-of-interest includes a plasmid comprising a gene encoding the polypeptide under the control of an inducible promoter. In some embodiments, the biomolecule-of-interest is a cytoplasmic polypeptide. In some embodiments, the biomolecule-of-interest is a polypeptide that includes a tag to facilitate binding to a substrate. In some embodiments, the encapsulation material includes chitosan, alginate, hyaluronic acid, polyethylene glycol polymers, polyethylene oxide polymers, elastin-like polypeptides (ELPs), resilin-like polypeptides (RLPs), or any derivatives or combinations thereof. In some embodiments, the encapsulation material is responsive to one or more conditions in the microcapsules. In some embodiments, the functional coupling of the microcapsules to the genetic circuit includes the plurality of microorganisms altering the one or more conditions in the microcapsules. In some embodiments, the one or more conditions in the microcapsules include pH or ionic strength. In some embodiments, the microorganisms are present in the microcapsules at a concentration from about $10^2$ to about $10^{10}$. In some embodiments, the system further includes a microfluidics platform to facilitate the production, purification, and/or analysis of the biomolecule-of-interest. In some embodiments, the microfluidics platform includes an input channel, a production chamber, and an assay chamber.

Embodiments of the present disclosure also include a microfluidics platform for biomolecule production. In accordance with these embodiments, the platform includes a microfluidic device comprising an input channel, a production chamber, and an assay chamber, a plurality of genetically engineered microorganisms comprising a genetic circuit and means for producing a biomolecule-of-interest, wherein the genetic circuit facilitates autonomous production of the biomolecule-of-interest; and an encapsulation material, wherein the encapsulation material is capable of forming microcapsules to contain the plurality of genetically engineered microorganisms, and wherein the microcapsules are functionally coupled to the genetic circuit.

In some embodiments, the production chamber is fluidly coupled to the input channel and the assay chamber. In some embodiments, the plurality of genetically engineered microorganisms are contained in the production chamber. In some embodiments, the device further includes an output channel fluidly coupled to the assay chamber or the production chamber. In some embodiments, the device includes a second input channel fluidly coupled to the assay chamber. In some embodiments, the production chamber is fluidly coupled to a purification chip. In some embodiments, the inner surface of the purification chip is modified to bind the biomolecule-of-interest.

Embodiments of the present disclosure also include a method for producing a biomolecule-of-interest. In accordance with these embodiments, the method includes loading a plurality of genetically engineered microorganisms contained in microcapsules into a microfluidics device, wherein the plurality of genetically engineered microorganisms include a genetic circuit and means for producing a biomolecule-of-interest; providing nutrients to the plurality of microorganisms; and producing the biomolecule-of-interest.

In some embodiments, the plurality of genetically engineered organisms includes bacteria or yeast. In some embodiments, the biomolecule-of-interest is at least one of a peptide, a polypeptide, a protein, a nucleic acid, a polynucleic acid, a DNA molecule, a RNA molecule, or any derivatives or combinations thereof. In some embodiments, the microcapsules include an encapsulation material comprising chitosan, alginate, or any derivatives or combinations thereof. In some embodiments, the microfluidics device includes an input channel, a production chamber, and an assay chamber.

BRIEF DESCRIPTION OF THE DRAWINGS

FIG. 2A: Programmed autonomous lysis by the ePop circuit (Top: circuit logic; bottom: experimental data). A density-dependent increase in plasmid copy number led to an increase in the expression of a toxin (the E protein from phage phiX174). At a sufficiently high concentration, the E protein caused cell lysis, leading to a decrease in the cell density. When turned ON (red curve), the circuit generated oscillations in the culture density of MC4100Z1 (ePop). The circuit can be turned OFF (green curve) by adding 1% glucose.

FIG. 2B: Shrinking of capsules in response to growth of encapsulated bacteria (Top: schematic; bottom: experimental data). MC4100Z1 cells carrying the ePop circuit and a constitutive GFP circuit (MC4100Z1(ePop/GFP)) were encapsulated in chitosan capsules and cultured in M9 culture medium. All data were normalized by the value at time zero. Inset: Microscopy images of MSBs at time 0 (left) and 48 (right) hours.

FIG. 2C: Growth-mediated capsule shrinking facilitates export of macromolecules from the capsules (Top: schematic; bottom: experimental data). MG1655 cells and Dextran-Rhodamine (Mw about 70000 g/mol) were encapsulated in chitosan capsules and cultured in M9 medium. Capsules were treated with or without ampicillin (100 μg/mL). Shrinking capsules, caused by bacterial growth in the absence of the antibiotics, led to about 2.25-fold increase in the rhodamine fluorescence in comparison with non-shrinking capsules after 24 hours, which contained non-growing bacteria (suppressed by antibiotic). Experiments were done in triplicate.

FIG. 3A: Protein production by programmed bacterial lysis can be taken over by mutants. As shown, at a high density, wild type cells (W) will autonomously lyse and release a product. A mutant (M) can arise spontaneously. M does not lyse thus does not contribute to protein production. In each environment, M will eventually dominate the culture.

FIG. 3B: As shown, a bulk culture is prone to complete mutant takeover. Once a mutant arises, it has access to the entire culture.

FIG. 3C: Encapsulation-mediated segregation delays mutant takeover. As shown, the small population size in each microcapsule reduced the probability by which mutants can emerge in each microcapsule. When a mutant emerges, it is confined within a capsule and will not contaminate the other encapsulated populations.

FIG. 3D: Results confirmed that segregation enhanced circuit stability. Equal amounts of MC4100Z1 (ePop) cells were inoculated in liquid culture or encapsulated inside the capsules with the same nutrients supply (M9 medium). After 24, 48 or 72 hours, the cells were collected from either culture and plated onto agar plates. About 10 clones were picked and tested for the maintenance of ePop function in LB medium containing no glucose. For each condition, the genetic stability was calculated as the percentage of the cells maintaining the ePop function (percentage of wide type). The experiments were done in triplicate.

FIG. 3E: An increase in the lysis rate (by decreasing glucose concentration) led to decreased genetic stability. MC4100Z1 (ePop) cells were inoculated in liquid culture or encapsulated inside the capsules, with the same amount of nutrients supply (M9 medium). The lysis rate was adjusted by controlling glucose concentration in the M9 medium. Cells were collected on 72 hours separately, re-plated and tested for lysis function afterwards. About 10 clones were picked and tested for the maintenance of ePop function in LB medium containing no glucose. For each condition, the genetic stability was calculated as the percentage of the cells maintaining the ePop function (percentage of wide type). The experiments were done in triplicate.

FIG. 3F: Results confirmed greater protein yield from the MSB platform. MC4100Z1 (ePop/BlaM) cells were inoculated in liquid culture or encapsulated inside the capsules, with the same amount of nutrients supply (M9 medium) for 72 hours. For the MSB culture, glucose was supplemented to adjust the lysis rate. The yield of BlaM was calculated based on its reaction with fluorocilin. All the values were normalized by the bulk culture condition. Experiments were done in triplicate.

FIG. 4A: Microfluidic platform for controlling and analyzing protein synthesis and release from MSBs. As shown, the production chamber contains the MSBs encapsulating MC4100Z1 carrying the ePop circuit and an inducible BlaM (M4100Z1 (ePop/BlaM)). The BlaM was quantified in the assay chamber by supplying fluorocilin, which was converted by BlaM to a fluorescent product.

FIG. 4B: Flow pattern. As shown, the blue bar indicates the flow is ON. The program is designed as follow: no flow in the first 8 hours, then flow is turned ON (0.5 µL/min for 0.5 hours)/OFF (0 µL/min for 1.5 hour) in cycle. The culture medium is LB.

FIG. 4C: Size oscillation of the MSBs. MSB sizes were normalized by 8 hours.

FIG. 4D: Fluorescence in the assay chamber. The fluorescence in the reaction chamber was recorded by microscopy at different time points. The data was background corrected.

FIG. 5A: Integrated operation on a microfluidic chip. Instead of an assay chamber, the production chamber was connected to a purification chip, which included a serpentine channel glued to a glass-slide. The surface of the glass-slide was modified for binding to His-tagged proteins. When released from the production chamber, a His-tagged protein is trapped in the purification chip by binding to the modified glass surface. After washing with PBS, the protein can be recycled by flowing through the elution buffer.

FIG. 5B: Integrated production and purification of model proteins using the microfluidic chip. MSBs containing BL21 (DE3) carrying the ePop circuit and ELPs-GFP-His (BL21 (DE3) (ePop/ELPs-GFP-His)) were loaded with LB medium in the culture chamber of production chip. The crude was transported from production chip (output) to purification chip (input) directly by a Teflon tube. The total culture time was 24 hours before binding. The flow rate for binding is 0.5 µL/min. The purification step was monitored by fluorescence microscopy. The images presented the GFP channel image (excitation=488 nm, emission=520 nm) of serpentine channel before binding, after binding, and after elution.

FIG. 5C: Integrated operation on a bench using a syringe. A syringe was used as a culture chamber and the MSBs are loaded with culture medium. A 0.45 µm hydrophilic membrane filter was attached onto the tip of the syringe to avoid leaking and evaporation of culture medium. After a specific period of time, the crude was directly purified by flowing through a Ni-NTA resin packed column.

FIG. 5D: Integration of purification module using ELPs on bench. MSBs containing BL21(DE3) (ePop/ELPs-GFP-His) were loaded in a syringe with 10 mL medium (LB or M9 medium) and cultured for 24 hours. The crude was pushed through a syringe filter for His-tag chromatography purification. The resultant proteins were tested on the SDS-PAGE gel. From left to right, the samples were crude, without (−) and with (+) IPTG induction in LB and M9 medium; purified protein, without and with IPTG induction in LB and M9 medium.

FIG. 5E: Periodic dosing led to increased protein yield. (Left: schematic; Right: experimental data). MSBs containing BL21(DE3) (ePop/ELPs-GFP-His) were loaded in a syringe and cultured for 24 hours. The total nutrients and culture time were 3 mL LB medium and 72 hours. The nutrients were dispensed in a periodic manner (nutrients each time×number of dose). For the sample 3×1, 3 mL medium was supplemented at time 0 and collected on 72 hours. For the sample 1.5×2, 1.5 mL medium was supplemented at time 0 and collected on 36 hours; and another 1.5 mL was supplemented at time 36 and collected on 72 hours. The dosing was done in following procedure. The syringe was laid horizontally and MSBs were allowed to settle on the wall. The crude was pushed through the filter. The filter was then removed and new culture medium was drawn into the syringe. Finally, the filter was attached again. The resultant elution was tested on SDS-PAGE separately. The elution volume and loading sample volume was similar between two different dosing patterns.

FIG. 5F: Microfiltration purification. LCST (lower critical solution temperature) phase transition was triggered at room temperature. The mixture was load and filtered through a syringe coupled with a 0.2 µm HT Tuffryn® Membrane. The aggregates of ELPs or ELPs-tagged proteins were retained by a microfiltration membrane while the other contents in the solution were washed away using a high-salt buffer at room temperature. To elute the aggregated ELPs, D.I. water was injected through the filter to reverse the LCST phase transition of the ELPs.

FIG. 5G: Purifying ELPs-tagged protein through microfiltration purification. Exogenous ELPs (5 µM) and NaCl (2 M) were added to trigger the LCST phase transition of the crude. The crude was then loaded and filtered through a syringe coupled with a 0.2 µm HT Tuffryn® Membrane. To elute the aggregation, D.I. water was injected through the filter. The left band shows the elution sample before His-tag purification. The right band shows the elution sample after His-tag purification.

FIG. 5H: Purifying two His-tagged proteins from crude by integrating microfiltration and affinity chromatography. Exogenous ELPs (5 µM) and NaCl (2 M) were added to trigger the LCST phase transition of the crude containing ELPs-GFP-His (POI1) and His-AAA (POI2). The crude was then purified through the microfiltration. The POI' was retained as aggregates while P012 was filtered through as soluble component. The aggregated ELPs were later dissolved and eluted by adding D.I. water to reverse the LCST phase transition of the ELPs. His-tag purification was carried out on both the elution portion (containing POI1) and the filtered portion (containing POI2). The purified result was tested on SDS-PAGE gel, with left band showing POI1, and right band showing P012.

FIG. 7A: Experimental measurements of the ePop dynamics. The genetic circuit generated population-level oscillations in MC4100Z1 cells when cultured in LB medium at 37° C. As shown, the lysis rate can be adjusted by supplementing with various glucose concentrations (w/v), as indicated.

FIG. 7B: ePop dynamics in multiple cell strains. The circuit generated population-level oscillations in multiple strains when cultured in LB medium at 37° C., as indicated.

FIG. 7C: Microcapsule sizes as a function of time during bacterial growth. Chitosan capsules encapsulating MG1655 were cultured in LB (red) or M9 (green) medium at 37° C. The sizes were normalized at time zero.

FIG. 7D: Shrinking of chitosan capsules due to cell growth increases the export of macromolecules. MG1655 cells and Dextran-Rhodamine (Mw about 70000 g/mol) were encapsulated in the chitosan capsules or alginate capsules, and cultured in LB or M9 medium at 37° C. Capsules were treated with or without ampicillin (100 μg/mL). The rhodamine fluorescence in the medium of capsules with non-growing bacteria (suppressed by antibiotic) is considered as basal level transportation, which is highly related with structure of the capsules. Therefore, the transportation capability of two different capsules was calculated as the ratio of rhodamine fluorescence in the medium after 24 hours with and without cell growth (normalization). Experiments were done in triplicate.

FIG. 8A: Modeling ePop-mediated production of protein-of-interest (POI) by accounting for mutant generation. After encapsulation, growing volume was dispensed into k capsules. Carrying capacity of all capsule was assumed to be equal to the bulk culture and the same total nutrients. The initial cell density in one capsule was the value for bulk culture divided by k. In the model, k was given the value of 100.

FIG. 8B: Experimental protocol to compare the genetic stability of the ePop circuit in a bulk culture and an MSB culture. Equal amounts of cells were inoculated into bulk culture or encapsulated into the capsules and supplemented with the same amount of nutrients. After a certain period of time, the cells were collected from either culture and evaluated for ePop circuit function. The percentage of the cells maintaining the circuit function indicated the genetic stability of the ePop circuit for the conditions.

FIG. 8C: Simulation predicts that segregation enhances stability of the ePop circuit. The x-axis shows different lysis rates. The y-axis presents the gene stability. A threshold was set for the mutant population. The gene stability was calculated as the ratio of the time when the mutant population surpasses the threshold and the entire time span. Red and green data points presented the bulk and segregation state, respectively.

FIG. 8D: Simulation predicts that, from the same amount of medium, the protein yield from MSB is greater than that from a bulk culture due to higher circuit stability. Simulation results of protein production with mutant for bulk or segregation state at different lysis rates are shown. When the lysis rate is too small, too little protein is released; when the lysis rate is too large, the population is quickly dominated by mutants, again leading to a reduction in the protein yield. Red and green data points presented the bulk and segregation state, respectively.

FIG. 9A: Functional tests of BlaM coupled with ePop circuit. MC4100 cells sensitive to carbenicillin were spread on top of the agar plate containing carbenicillin. The supernatants of the overnight cultures of E. coli MC4100 were added in different wells: 1—samples from the cells not carrying the ePop circuit and not expressing BlaM (negative control); 2—from cells expressing BlaM but not carrying ePop; 3—from cells carrying the ePop and expressing BlaM. As indicated, only the sample placed in well 3 led to the rescue of the sensitive cells spread on the agar due to the presence of the effector BlaM, degrading the antibiotic and thus allowing sensitive MC4100 cells to survive (halo around well 3).

FIG. 9B: Reaction of beta-lactamase and fluorocilin generates the fluorescence signal. MC4100Z1 (ePop/BlaM) cells were induced for gene expression. The medium was supplemented with 0% (lysis circuit ON) or 2% glucose (lysis circuit OFF). About 20 μL of collected supernatant was diluted 10 times by PBS and then mixed by enzymatic reaction with the substrate (2 μM). The y-axis shows the fluorescence readout for both samples. When the substrate is saturating, the initial slope of the fluorescence is proportional to the activity of the BlaM.

FIG. 10A: The ELPs (ELP4-80, 5 μM) experience thermal transition at about 33° C.

FIG. 10B: The typical inverse transition cycling involves multiple rounds of temperature adjustment and centrifuge.

FIG. 10C: Phase transition of the crude occurred at room temperature with addition of exogenous ELPs (left) at high sale concentration (NaCl 2 M). The solution was clear (Right) without exogenous ELPs (5 μM) at same salt concentration (NaCl 2 M).

FIG. 11A: Multiple ELPs fused with Spytag/Spycatcher are expressed in the MSB platform. From left to right, they are AAA (SpyTag-Elastin-SpyTag-Elastin-SpyTag), BBB (SpyCatcher-Elastin-SpyCatcher-Elastin-SpyCatcher), AA-mcherry (SpyTag-Elastin-mCherry-Elastin-SpyTag) and BB (SpyCatcher-Elastin-RGD-Elastin-SpyCatcher), which were expressed under a T5 promoter with p15A replication of origin.

FIG. 11B: Multiple RLPs tagged proteins were expressed in the MSB platform. From left to right, they are RLPs-GFP-His (p15A/T7), RLP-2-GFP-His (p15A/T5) and RLP-3-GFP-His (p15A/T5).

FIG. 11C: Super uranyl binding protein (SUP) expressed and purified in the MSB platform.

FIG. 11D: Pigment-protein (PrancerPurple) expressed and purified in the MSB platform.

FIG. 11E: Enzyme (3A-BlaM) expressed and purified in the MSB platform.

FIG. 11F: Multiple therapeutic proteins were expressed and purified in the MSB platform. Left panel shows GLP-1-ELPs-His, and right panel shows Griffithsin-His (GRFT).

FIG. 12A: MSBs can be stored for long term without significant loss in performance. Equal amounts of MSBs were stored in either 4° C. or −80° C. for different periods ranging from 1 week to 8 weeks. After storage, they were resuspended in LB medium and cultured for 48 hours. Compared with control, which was made fresh and cultured for 48 hours, the MSBs stored in −80° C. had a comparable yield even after 8 weeks storage. Experiments were done in triplicate. All the values were normalized by controls.

FIG. 12B: Operation of the MSB platform is simple and convenient. The capsules (stored in −80° C.) were thawed in the room temperature and resuspend in nutrients. The culture was transferred to a syringe with a 0.45 µm hydrophilic membrane filter attached onto the tip to avoid leaking and evaporation of culture medium. For purification, a His-tag binding column was connected at the downstream, and the culture was pushed directly for binding.

FIG. 13A: Modify the surface of the capsules by Layer-by-Layer coating methodology. The chitosan particle is positively charged. Therefore, the modification was implemented by first depositing negatively charged alginate, followed by positively charged chitosan with wash steps in between.

FIG. 13B: The surface of the capsules turns from smooth to rough after modification. These microcapsules were imaged in bright-field view. From left to right, they are before modification, only alginate deposited, and LbL modification capsules.

FIG. 13C: The separation efficacy is largely improved with negligible effect on yield. Escape rate is defined as the percentage of the escape cells in terms of total cell number. It is calculated as dividing the number of the cells (MC4100Z1 (ePop/BlaM)) in the surrounding medium of MSB culture by the number of cells in the bulk culture after 24 hours incubation. After LbL modification, the escape rate of the cells decreased about 1000-fold compared with non-modification (left). To compare the yield, 20 µL medium in MSB culture (48 hours) was diluted into 200 µL using PBS and mixed with Fluorocillin™ Green (Thermo Fisher) to obtain a final substrate concentration of 2 µM. The LbL modification MSB showed a comparable yield comparing with the non-modification MSB (right). Measurements were done in triplicate.

FIG. 14A: Encapsulation and post-processing protocol. A homogeneous mixture of chitosan and cells/solution was transferred into a syringe with an attached blunt tip. The syringe was placed in an electrospray system equipped with a syringe pump. The anode of the electrospray system was connected to the needle and the cathode was connected to a sterile metal receiving container with crosslinking solution (5% TPP). The solution was sprayed at high voltage to the receiving container with gentle agitation.

FIG. 14B: Morphology and size of the chitosan capsules. A bacterium is about 1 µm in diameter. A microcapsule is about 300-400 µm in diameter.

FIG. 14C: Encapsulation of MG1655 cells constitutively expressing GFP. These microcapsules were imaged in phase and GFP channels after incubation at 37° C. in M9 medium for 24 hours.

DETAILED DESCRIPTION

Figure 1:
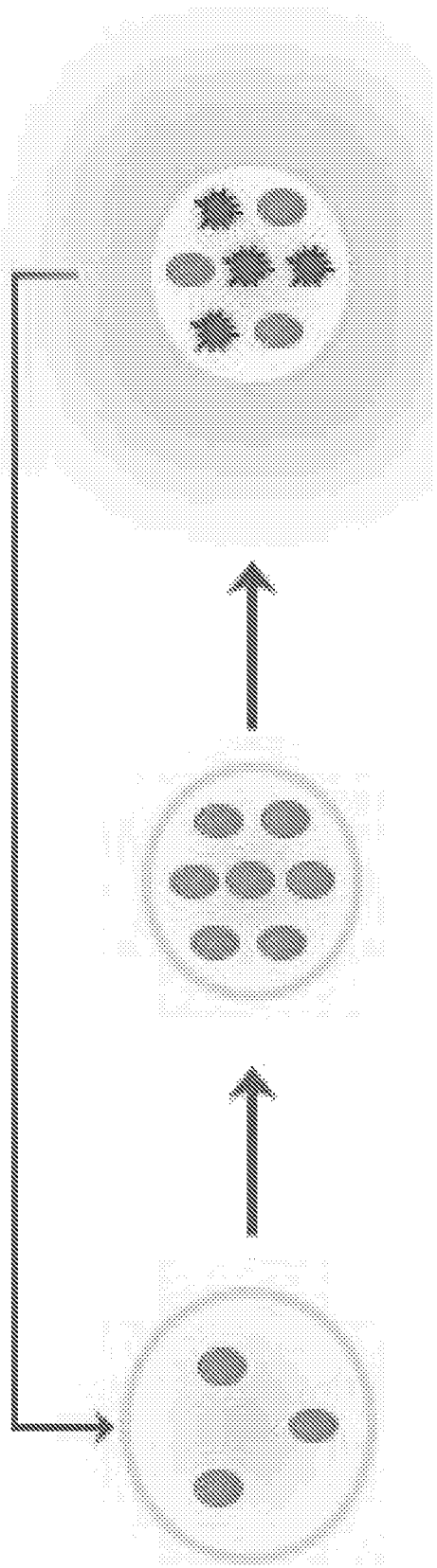
FIG. 1 includes a representative schematic of the design concept of a Microbial swarmbot (MSB) platform for biomolecule production, according to the present disclosure. Each swarmbot includes of a small population of engineered bacteria encapsulated in polymeric microcapsules. As shown, bacteria can be engineered to undergo partial lysis at a sufficiently high local density. Conversely, the encapsulating material can shrink in response to the changing chemical environment caused by cell growth. As the bacteria undergo programmed autolysis, they release intracellular proteins. The crosslinked polymeric capsules trap the living cells and large debris inside, and the corresponding shrinking facilitates the export of protein products from the capsules. The system is reset by replenishing with fresh medium.

The present disclosure provides compositions, systems, and methods relating to the production of biomolecules using microorganisms. In particular, the present disclosure provides biomolecule production platforms that include genetically engineered microorganisms with genetic circuits functionally coupled to microcapsules formed from materials that are responsive to culture conditions. The biomolecule production platforms disclosed herein facilitate the efficient and robust production, purification, and/or analysis of any biomolecule-of-interest.

Small-scale production of biologics has great potential in facilitating individualized medicine and enhancing the accessibility of biomanufacturing. By exploiting cell-material feedback, a concise platform to achieve versatile production, analysis, and purification of diverse proteins was developed. The core of the technology described in the present disclosure is a microbial swarmbot, which includes a stimulus-sensitive polymeric microcapsule encapsulating engineered bacteria. By sensing the confinement, the bacteria undergo programmed partial lysis at a high local density. Conversely, the encapsulating material shrinks in response to the changing chemical environment caused by cell growth and death, squeezing out the protein products released from bacterial lysis. This platform was then integrated with downstream quantification of enzymatic kinetics and diverse modes of protein purification. Embodiments presented herein demonstrate the use of the feedback between living cells and materials to engineer a modular and flexible platform with a sophisticated programmed function.

Bacteria are a common host to produce diverse biologics, accounting for about 30% of biopharmaceuticals. Synthesis of recombinant proteins using bacterial hosts entails multiple steps including culturing, disruption of bacteria by physical or chemical means, and subsequent isolation and purification of the desired product. For industrial operations, these steps are usually carried out on a large scale; consequently, each step requires a sophisticated and delicate infrastructure to ensure efficiency and product quality. While this may be important for producing molecules in large amounts, this format is not flexible or economically suited for producing diverse biologics when only a small amount is needed for each. Moreover, standard biomanufacturing is not accessible in remote or underdeveloped areas that lack the basic infrastructure (e.g., transportation, equipment, or electricity) and personnel with necessary technical training. Conventional manufacturing of certain products in advance could also result in wasted labor and resources due to the high cost of production, the need for a cold chain for transportation and storage, and the short shelf-life of biologics. Therefore, there is a need to develop technologies for versatile and scalable production of diverse biologics on demand, as well as subsequent analysis and purification.

This need has motivated the development and adoption of single-use technologies (SUTs) for biomanufacturing. To date, however, the SUTs have focused on replacing traditional stainless steel-based fixed reactors with flexible and disposable parts or the direct miniaturization of reactors, without changing the fundamental structure of the manufacturing process. In particular, distributing production of biologics into multiple steps is a standard practice and important for implementing the production and purification as unit operations, where each unit operation can be individually optimized for large-scale biomanufacturing. However, each step can lead to an opportunity for product loss and thus reduced efficiency, particularly for small-scale operations. During biopharmaceutical manufacturing operating costs, 75%-80% of the total cost is spent on the downstream processing, including the disruption of cells, subsequent separation, clarification and purification of target products. For certain proteins, engineered secretion can facilitate the extraction process. Yet, the diverse secretion mechanism of bacteria makes the selection of the appropriate secretion pathway for each recombinant protein complicated and time consuming. Besides, the efficiency of secretion is often limited in bacterial hosts, and some large cytoplasmic proteins may be physically impossible to translocate. Induced lysis can allow effective release of diverse proteins, but it does not simplify the process of cell debris separation and downstream purification.

To overcome these limitations, we combine aspects of synthetic biology and stimulus-responsive biomaterials to integrate the multiple steps of production, disruption and separation into a concise format. Embodiments of the present disclosure couple programmed lysis of engineered bacteria and controlled periodic capsule phase transition. When the local cell density inside the capsule is sufficiently high, autonomous partial lysis will occur and allows the cells to release their contents, including the protein product of interest. The bacterial growth can alter the local environmental conditions (e.g., pH and ionic strength), driving the phase transition of the encapsulating material. Consequently, in some embodiments, the released protein is transported from the interior to exterior with shrinking of the growth-sensitive capsule, while cells and large debris are trapped inside the capsules. In accordance with these embodiments, nutrient replenishment can be used as a cue to allow the capsule to swell again, while it resets the capsule environment, and also allows the cell density to begin increasing after it drops to a certain level. The interplay between sustained partially lysis of engineered bacteria and periodic phase transition of the encapsulating material enables sustained product synthesis and separation.

Figure 6:
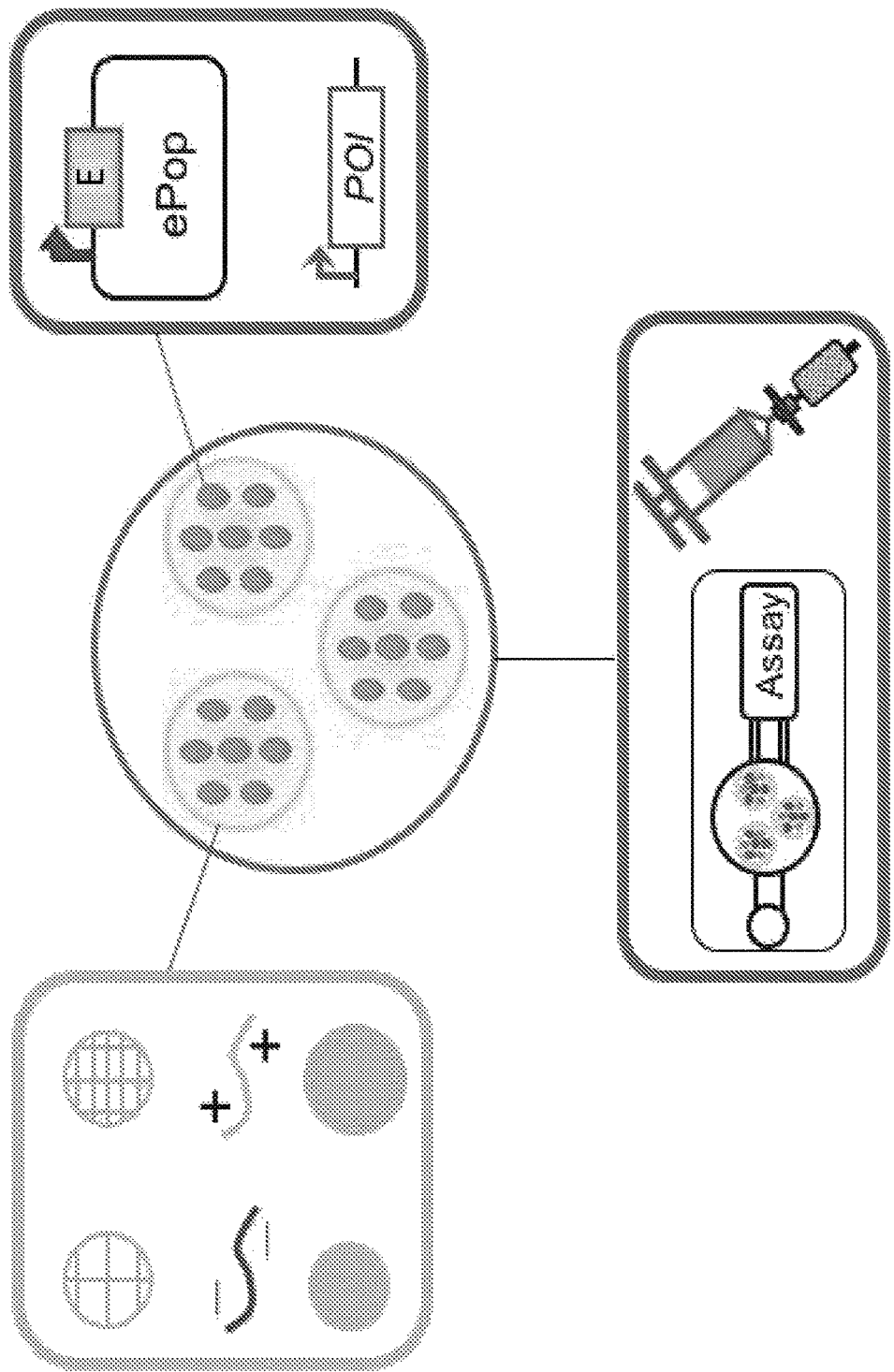
FIG. 6 includes a representative schematic illustrating the modularity and flexibility of the MSB platform of the present disclosure. The core of the platform is the MSBs. To program autonomous lysis, the ePop circuit can be replaced by other circuits and optimized in various host trains; and versatile POIs can be expressed (right). The separation is obtained by chitosan-based microcapsules, which can be replaced by other encapsulating materials with different physical and chemical properties, including different cross-linking density; charge property and proper surface modification (left).

The biomolecule production systems of the present disclosure demonstrate the use of active feedback control mediated by the interplay between engineered bacteria and stimulus-responsive materials, and facilitate integrated protein synthesis, separation, and downstream processing. This design enables the development of a completely novel format of SUT for distributed biomanufacturing. By design, the biomolecule production systems of the present disclosure are modular and scalable: the engineered gene circuit, the host strain, the target product, the encapsulating material and downstream processing (e.g., FIG. 6) can be separately optimized and then integrated, depending on the application context. The ePop circuit can also be replaced with other circuits able to program autolysis or integrated with cell-free-based systems. Similar design concepts can be implemented with appropriate gene circuits in different bacterial and yeast hosts. Compared with cell-free systems, the use of living cells has the advantage of higher expression efficiency. Due to the release mechanism build into MSB, the biomolecule production platforms of the present disclosure are not limited to proteins that have to be secreted by living cells.

Figures 13A, 13B:
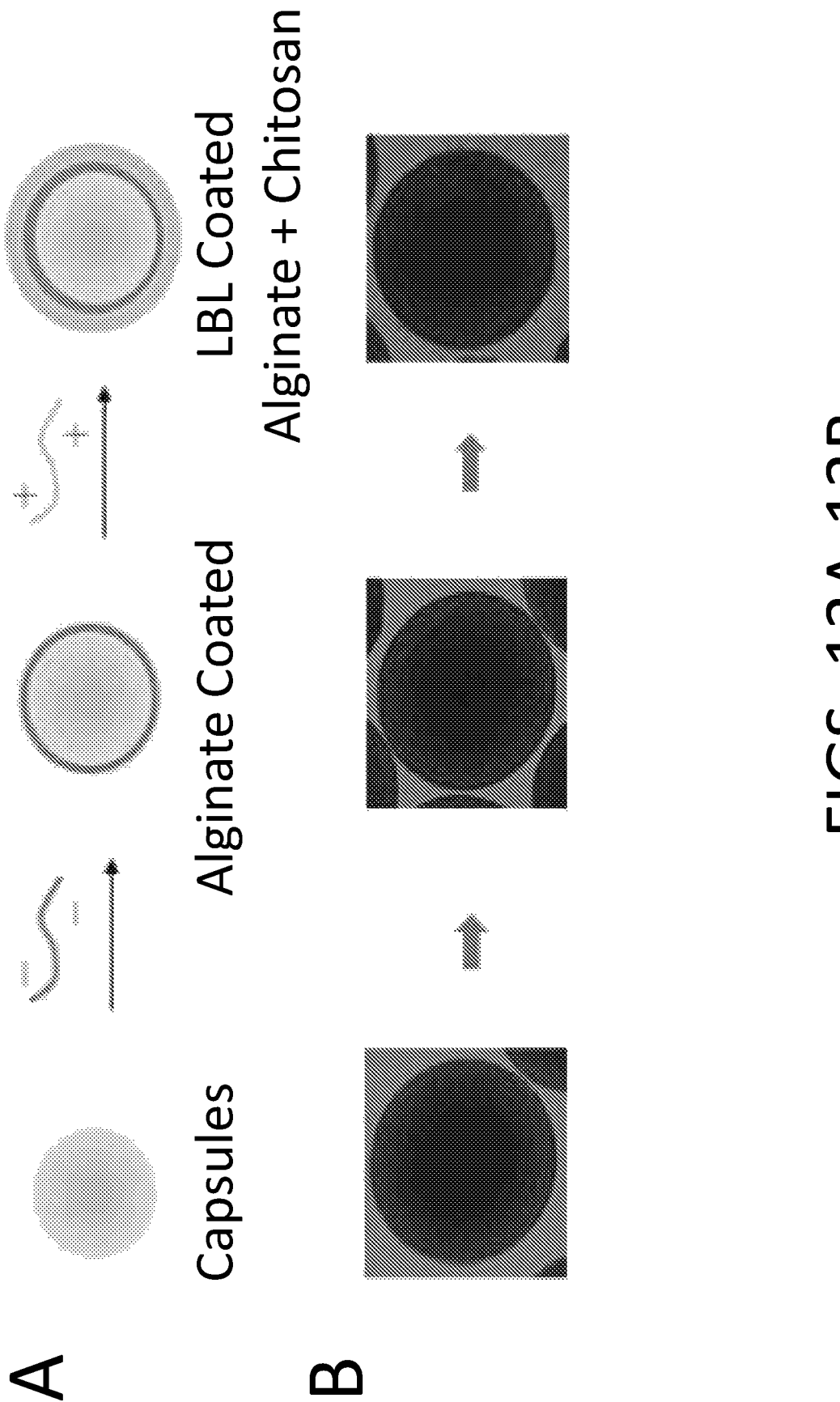
FIGS. 13A-13C include representative results demonstrating that surface modification can further increase the separation efficacy with negligible effect on yield.
Figure 13C:
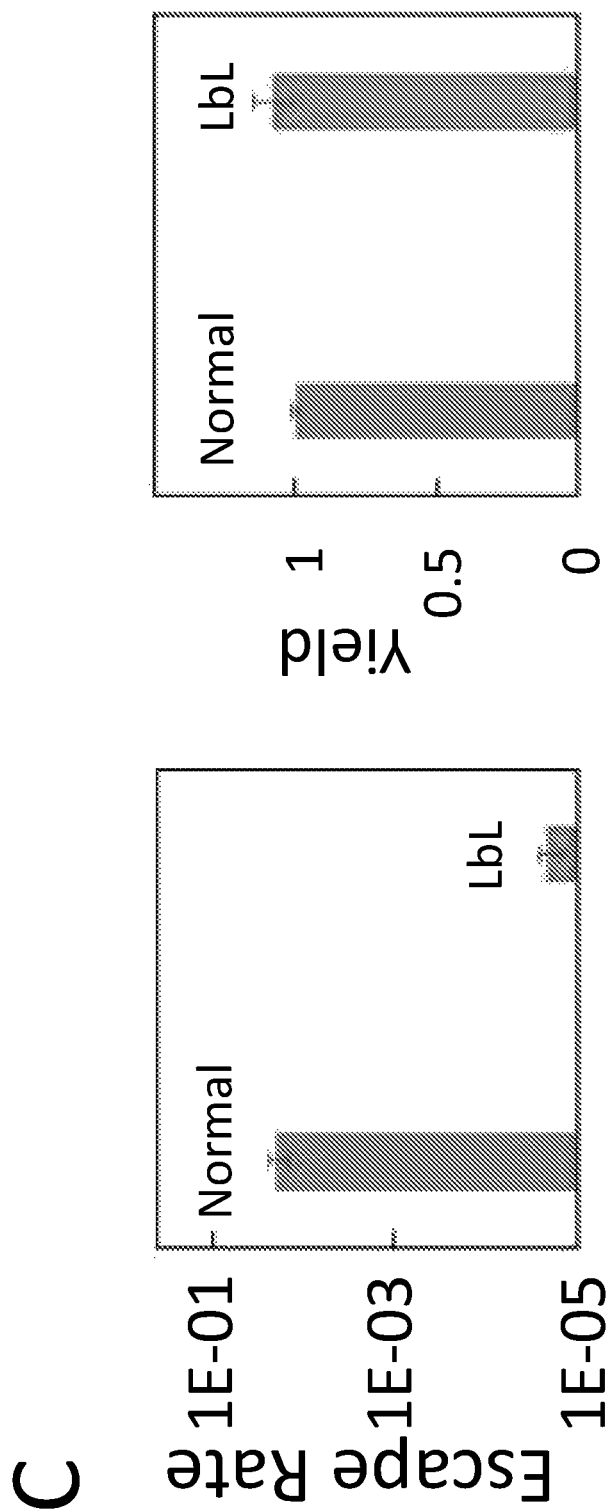

Polymeric capsules provide physical support to the living cells and restrain the free diffusion of cells and large debris. Chitosan was used in this study in part due to its well-established stimulus responsiveness. Its stability facilitates the preparation of MSBs in advance and enables long-term storage with negligible decrease in performance. In general, other stimulus-responsive materials can be adopted to fine-tune biocompatibility, durability, and separation capability. For example, capsules with different pore sizes or charge properties can enable more selective purification of macromolecules. Also, the separation and clarification function could be further enhanced by surface modification on the polymeric capsules (FIG. 13). As described herein, a layer-by-layer coating technique was applied to modify the surface of the capsules with a thin layer of polycations. This modification significantly decreases the escape rate of the cells by about 1000-fold, with no significant loss in the yield in LB medium culture (FIG. 13C). The escape rate of the cells is nearly zero in M9 medium culture after 24 hours for modified MSB.

Section headings as used in this section and the entire disclosure herein are merely for organizational purposes and are not intended to be limiting.

1. DEFINITIONS

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present disclosure. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

"Correlated to" as used herein refers to compared to.

"Identical" or "identity," as used herein in the context of two or more polypeptide or polynucleotide sequences, can mean that the amino acid or nucleotide sequences have a specified percentage of residues that are the same over a specified region. The percentage can be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of the single sequence are included in the denominator but not the numerator of the calculation.

"Isolated polynucleotide" as used herein may mean a polynucleotide (e.g., of genomic, cDNA, or synthetic origin, or a combination thereof) that, by virtue of its origin, the isolated polynucleotide is not associated with all or a portion of a polynucleotide with which the "isolated polynucleotide"

is found in nature; is operably linked to a polynucleotide that it is not linked to in nature; or does not occur in nature as part of a larger sequence.

"Peptide" refers an oligomer to short polymer of amino acids linked together by peptide bonds. In contrast to other amino acid polymers (e.g., proteins, polypeptides, etc.), peptides are of about 50 amino acids or less in length. A peptide may comprise natural amino acids, non-natural amino acids, amino acid analogs, and/or modified amino acids. A peptide may be a subsequence of naturally occurring protein or a non-natural (artificial) sequence.

"Polypeptide" refers to a polymer of amino acids linked together by peptide bonds that is greater than about 50 amino acids in length. Polypeptides may comprise natural amino acids, non-natural amino acids, amino acid analogs and/or modified amino acids, and may be a naturally occurring sequence, or a non-natural (artificial) sequence, or a subsequence of naturally occurring protein or a non-natural (artificial) sequence. "Artificial" refers to compositions and systems that are designed or prepared by man, and are not naturally occurring. For example, an artificial sequence refers to an amino acid or nucleotide sequence that does not occur in nature (e.g., a polypeptide without 100% identity with a naturally-occurring protein or a fragment thereof). "Conservative" amino acid substitution refers to the substitution of an amino acid in a peptide or polypeptide with another amino acid having similar chemical properties, such as size or charge. For purposes of the present disclosure, each of the following eight groups contains amino acids that are conservative substitutions for one another:

1) Alanine (A) and Glycine (G);
2) Aspartic acid (D) and Glutamic acid (E);
3) Asparagine (N) and Glutamine (Q);
4) Arginine (R) and Lysine (K);
5) Isoleucine (I), Leucine (L), Methionine (M), and Valine (V);
6) Phenylalanine (F), Tyrosine (Y), and Tryptophan (W);
7) Serine (S) and Threonine (T); and
8) Cysteine (C) and Methionine (M).

Naturally occurring residues may be divided into classes based on common side chain properties, for example: polar positive (or basic) (histidine (H), lysine (K), and arginine (R)); polar negative (or acidic) (aspartic acid (D), glutamic acid (E)); polar neutral (serine (S), threonine (T), asparagine (N), glutamine (Q)); non-polar aliphatic (alanine (A), valine (V), leucine (L), isoleucine (I), methionine (M)); non-polar aromatic (phenylalanine (F), tyrosine (Y), tryptophan (W)); proline and glycine; and cysteine. As used herein, a "semi-conservative" amino acid substitution refers to the substitution of an amino acid in a peptide or polypeptide with another amino acid within the same class.

"Variant" is used herein to describe a peptide or polypeptide that differs in amino acid sequence by the insertion, deletion, or conservative substitution of amino acids, but retain at least one biological activity. "SNP" refers to a variant that is a single nucleotide polymorphism. Representative examples of "biological activity" include the ability to be bound by a specific antibody or to promote an immune response. Variant is also used herein to describe a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree, and distribution of charged regions) is recognized in the art as typically involving a minor change. These minor changes can be identified, in part, by considering the hydropathic index of amino acids, as understood in the art. Kyte et al., *J. Mol. Biol.* 157:105-132 (1982). The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. U.S. Pat. No. 4,554,101, incorporated fully herein by reference. Substitution of amino acids having similar hydrophilicity values can result in peptides retaining biological activity, for example immunogenicity, as is understood in the art. Substitutions may be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

"Vector" is used herein to describe a nucleic acid molecule that can transport another nucleic acid to which it has been linked. One type of vector is a "plasmid", which refers to a circular double-stranded DNA loop into which additional DNA segments may be ligated. Another type of vector is a viral vector, wherein additional DNA segments may be ligated into the viral genome. Certain vectors can replicate autonomously in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. "Plasmid" and "vector" may be used interchangeably as the plasmid is the most commonly used form of vector. However, other forms of expression vectors, such as viral vectors (e.g., replication defective retroviruses, adenoviruses and adeno-associated viruses), which serve equivalent functions, can be used. In this regard, RNA versions of vectors (including RNA viral vectors) may also find use in the context of the present disclosure.

Unless otherwise defined herein, scientific and technical terms used in connection with the present disclosure shall have the meanings that are commonly understood by those of ordinary skill in the art. For example, any nomenclatures used in connection with, and techniques of, cell and tissue culture, molecular biology, immunology, microbiology, genetics and protein and nucleic acid chemistry and hybridization described herein are those that are well known and commonly used in the art. The meaning and scope of the terms should be clear; in the event, however of any latent ambiguity, definitions provided herein take precedent over any dictionary or extrinsic definition. Further, unless otherwise required by context, singular terms shall include pluralities and plural terms shall include the singular.

2. MICROORGANISMS

Embodiments of the present disclosure include the use of microorganisms for biomolecule production. In accordance with these embodiments, systems and platforms for biomolecule production include a plurality of genetically engineered microorganisms comprising a genetic circuit and means for producing a biomolecule-of-interest. In some embodiments, microorganisms include various strains of bacteria and yeast (including both probiotic and non-probiotic strains). In some embodiments, various E. coli strains are used, given their genetic diversity and robust use in biomolecule production. Bacterial strains that can be used in the biomolecule platforms and systems of the present disclosure include, but are not limited to, E. coli strains such as MC4100 (e.g., MC4100Z1), MG1655, BL21 (e.g., BL21 (DE3)), NISSLE1917, and any variant or derivative strains thereof. Other bacterial strains that can be used are included in Table 1 below.

TABLE 1

*E. coli* expression strains.

| Strain | Resistance | Key Features | Genotype | Use |
| --- | --- | --- | --- | --- |
| BL21 (DE3) | | Basic IPTG-inducible strain containing T7 RNAP (DE3) | F- ompT lon hsdSB (rB- mB-) gal dcm (DE3) | General protein expression |
| BL21 (DE3) pLysS* | Chloramphenicol (pLysS) | pLysS expresses T7 lysozyme to reduce basal expression levels; expression vector cannot have p15A origin of replication | F- ompT lon hsdSB (rB- mB-) gal dcm (DE3) pLysS (CamR) | Expression of toxic proteins |
| BL21 (DE3) pLysE* | Chloramphenicol (pLysE) | pLysE has higher T7 lysozyme expression than pLysS; expression vector cannot have p15A origin of replication | F- ompT lon hsdSB (rB- mB-) gal dcm (DE3) pLysE (CamR) | Expression of toxic proteins |
| BL21 star (DE3) | | Lacks functional RNaseE which results in longer transcript half-life | F- ompT lon hsdSB (rB- mB-) gal dcm rne131 (DE3) | General expression; not recommended for toxic proteins |
| BL21-A1 | Tetracycline | Arabinose-inducible expression of T7 RNAP; IPTG may still be required for expression | F- ompT lon hsdSB (rB- mB-) gal dcm araB::T7RNAP-tetA | General protein expression |
| BLR (DE3) | Tetracycline | RecA-deficient; best for plasmids with repetative sequences. | F- ompT lon hsdSB (rB- mB-) gal dcm (DE3) Δ(srl-recA)306::Tn10 (TetR) | Expression of unstable proteins |
| HMS174 (DE3)** | Rifampicin | RecA-deficient; allows for cloning and expression in same strain | F- recA1 hsdR(rK12- mK12+) (DE3) (RifR) | Expression of unstable proteins |
| Tuner (DE3) | | Contains mutated lac permease whch allows for linear control of expression | F- ompT lon hsdSB (rB- mB-) gal dcm lacY1 (DE3) | Expression of toxic or insoluble proteins |
| Origami2 (DE3)** | Streptomycin and Tetracycline | Contains highly active thioredoxin reductase and glutathione reductase to faciliate proper folding; may increase multimer formation | Δ(ara-leu)7697 ΔlacX74 ΔphoA PvuII phoR araD139 ahpC galE galK rpsL F'[lac+ lacIq pro] (DE3) gor522::Tn10 trxB (StrR, TetR) | Expression of insoluble proteins |
| Rosetta2 (DE3)* | Chloramphenicol (pRARE) | Good for "universal" translation; contains 7 additional tRNAs for rare codons not normally used in E. coli. Expression vector cannot have p15A origin of replication | F- ompT lon hsdSB (rB- mB-) gal dcm (DE3) pRARE2 (CamR) | Expression of eukaryotic proteins |
| Lemo21 (DE3)* | Chloramphenicol (pLemo) | Rhamnose-tunable T7 RNAP expression alleviates inclusion body formation. Expression vector cannot have p15A origin of replication | fhuA2 [lon] ompT gal (λ DE3) [dcm] ΔhsdS/pLemo (CamR) | Expression of toxic, insoluble, or membrane proteins |
| T7 Express | | IPTG-inducible expression of T7 RNAP from the genome; does not restrict methylated DNA | fhuA2 lacZ::T7 gene1 [lon] ompT gal sulA11 R(mcr-73::miniTn10--TetS)2 [dcm] R(zgb-210::Tn10--TetS) | General protein expression |
| m15 pREP4*, ** | Kanamycin (pREP4) | Cis-repression of the E. coli T5 promoter (found on vectors such as pQE or similar), inducible under IPTG (lac repressor on the pREP4 plasmid). Expression vector cannot have p15A origin of replication | F-, Φ80ΔlacM15, thi, lac-, mtl-, recA+, KmR | Expression of toxic proteins |

In some embodiments, various strains of yeast can be used with the biomolecule production platforms and systems of the present disclosure. These include, for sample, strains from the genera *Saccharomyces, Pichia, Kluyveromyces, Hansenula* and *Yarrowia*.

Other microorganisms can also be used, as would be recognized by one of ordinary skill in the art based on the present disclosure.

3. GENETIC CIRCUITS

Embodiments of the present disclosure include the use of microorganisms for biomolecule production that include one or more genetic circuits. Genetic circuits can include one or more modules for carrying out various functions, such as biomolecule production. For example, as described herein, the ePop genetic circuit comprises a cell lysis module (e.g., based on a gene encoding E protein from phage phiX174) and a cell density sensing module (e.g., based on a mutated luxR gene and a ColE1 origin of replication lacking the Rom/Rop protein), which facilitate autonomous biomolecule production. In accordance with these embodiments, engineered ePop circuits can be used to program autonomous lysis. The circuits can be configured to exploit the cell-density dependent copy number control in ColE1-type plasmids that is coupled to leaky expression of a toxin (see, e.g., FIG. 2A). High cell densities can lead to an increase in plasmid copy number and greater E protein expression, which then led to lysis of a subpopulation of the bacteria. Circuit dynamics are readily tunable by exogenously controlling one or more conditions of the culture media.

Genetic circuits can include any number of modules required to carry out a desired function, including but not limited to, sensing of cell density, and cell density-dependent cell lysis (e.g., triggered expression of any cell lysis mechanism, including expression of any gene/protein that can lead to cell lysis), as described herein. In some embodiments, cell density sensing and related functions can be based on quorum sensing systems, and can be used to generate one or more modules of a genetic circuit. Quorum sensing systems are well known in the art and can be the basis for generating genetic circuits in accordance with the methods and systems described herein (see, e.g., You, L. et al., *Nature*, 428: pp. 868-871 (22 Apr. 2004)).

As described herein, many other genetic circuits can be used as part of the biomolecule production platforms and systems of the present disclosure. As would be recognized by one of ordinary skill in the art based on the present disclosure, various genetic circuits can be created by exploiting the various biological processes in microorganisms, as summarized in Table 2 below (see, e.g., Bradley et al., Tools and Principles for Microbial Gene Circuit Engineering, J. of Mol. Biol. (2016): 428(5B), pp. 862-888).

TABLE 2

Bases for creating genetic circuits.

| Biological Process | Action | Basis |
|---|---|---|
| *Control of RNA levels* | | |
| Promoters (RNAP binding) | Control of transcription initiation rate | Activity can be reasonably well predicted with thermodynamic models but is sensitive to changes in adjacent sequences |
| *Transcriptional activators* | | |
| Extracytoplasmic function σ factors | Recruitment of RNAP to specific promoter sequences | 20 orthogonal ECF/promoter pairs characterized, all with cognate anti-σ factors |
| Bacterial enhancer binding proteins (HrpRS); chaperone activators; phage activators | Recruitment of RNAP to specific promoter sequences | HrpRS activate the σ54-dependent PhrpL; ATP dependency gives a low OFF state for a digital-like response |
| T7 RNAP | Single-subunit phage RNAP recognizes orthogonal promoters | Variants that recognize orthogonal promoter sequences exist; protein can be split to increase functionality |
| *Transcriptional repressors* | | |
| TetR homologues; LacI variants | DNA binding proteins (block promoter binding by RNAP) | 16 orthogonal TetR variants characterized with up to 200-fold repressive activity |
| TALE repressors | DNA binding proteins with programmable sequence specificity | Construction of TALE proteins is relatively time consuming |
| *Small-molecule inducible control of transcription* | | |
| Riboswitches | Cis-elements that control transcription termination | Only a few small molecules can be sensed |
| UAA control of transcription | UAA availability controls ribosome stalling in a leader peptide | Positive regulation is based on tna operon control; negative regulation uses trp operon attenuator |
| Optogenetics | Light-sensing two-component systems | Can specifically detect red, green, or blue wavelength |
| *RNA control of transcription* | | |
| pT181-based transcription repression | A taRNA induces formation of a transcription terminator | Cis-elements can be concatenated |
| STARs | A taRNA disrupts formation of a transcription terminator | Up to 94-fold dynamic range |

TABLE 2-continued

Bases for creating genetic circuits.

| Biological Process | Action | Basis |
|---|---|---|
| tna adapter | Transcriptional regulation via translational regulation of tna leader peptide synthesis | $10^3$-fold dynamic range when combined with the IS10 translational regulator |
| CRISPR-dCas9 transcriptional regulation | | |
| dCas9 transcription repression | Repression of transcription initiation or elongation | Programmable sgRNA directs dCas9 to specific sequences for $10^3$-fold repression |
| dCas9:RNAP ω transcription activation | Recruitment of RNAP ω subunit to promoter enhances transcription initiation | Largest impact observed with weak promoters |
| RNA degradation | | |
| Csy4 cleavage | Csy4 endoRNase degrades target mRNA | Requires the Csy4 target sequence to be encoded within the open reading frame |
| Self-cleaving aptazyme | Ligand-responsive ribozyme encoded at the 3' end of mRNA | Modular design can incorporate different aptamers |
| Control of protein levels | | |
| RBSs | Control of translation initiation rate | In silico modelling has good predictive power |
| Orthogonal ribosomes | Modified 16S rRNA initiates translation only from cognate orthogonal mRNAs | Three additional orthogonal ribosomes are available |
| Riboswitches | mRNA secondary structure occludes the RBS in a ligand-dependent manner | A limited number of ligands can be sensed: temperature sensing is also possible |
| taRNAs | | |
| sRNAs | Antisense RNA binds mRNA to block RBS and promote degradation | Conceptually simple to design, can target native mRNAs |
| IS10 repression | taRNA binds to cis-region of mRNA to block RBS | Many sets containing two to seven orthogonal pairs exist; requires cis-element upstream of open reading frame |
| Toehold switches | Trigger RNA sequesters a branch of a translation inhibition hairpin in the mRNA | Dynamic range of up to 600-fold activation; very few constraints trigger/switch binding sequence |
| Protein degradation | | |
| (Inducible) ssrA-tagged degradation | SsrA tags target protein for degradation by ClpXP machinery | SspB chaperone activity can be induced to tune degradation rate |
| *M. florum* Lon degradation | *M. florum* Lon protease is orthogonal to *E. coli*; modified tags can be recognized by both ClpXP and Lon | Various steady-state and inducible degradation rates available |
| Beyond transcription and translational control | | |
| Protein splicing | Split intein used to form a peptide bond between two proteins | Two- and three-way splicing is possible |
| Protein cleaving | Can be used to release a sequestered factor | Example uses the tobacco etch virus protease |
| Protein scaffolds | Protein binding domains used to immobilize and organize enzymes | Stoichiometry and relative position on the scaffold can be controlled |
| RNA scaffolds | CRISPR guide RNAs or multi-dimensional RNA structures as scaffolds for protein binding | CRISPR guide RNAs can recruit proteins to DNA; multi-dimensional RNA scaffolds spatially organize metabolic pathways |
| Inducible association of proteins | Target proteins are fused to signal-responsive interacting domains | Interacting domains that respond to small molecules or light are available |
| DNA modification for memory | | |
| Recombinases | Recombinases flip a section of DNA | Memory elements can be nested or concatenated: excisions can be employed to reverse DNA flipping |
| Retron-encoded analogue memory | ssDNA produced in response to a signal is incorporated into the genome at a replication fork | DNA changes can be targeted to any unique sequence in the genome; recombination frequency is proportional to ssDNA expression level |

4. BIOMOLECULES

Embodiments of the present disclosure provide systems and platforms for biomolecule production using genetically engineered microorganisms (e.g., MSBs), as described herein. In accordance with these embodiments, biomolecules that can be produced using the methods, systems, and platforms described herein include, but are not limited to, peptides, polypeptides, proteins, nucleic acids, polynucleic acids, DNA molecules (double or single-stranded), RNA molecules (double or single-stranded), small molecule compounds, and any derivatives or combinations thereof.

In some embodiments, the biomolecule-of-interest is a protein-based molecule made of amino acids. Such proteins/peptides include, but are not limited to, enzymes, antibodies, peptide hormones, therapeutic biologics/biosimilars, immunomodulatory proteins, antigenic proteins, immunogenic proteins, cytoplasmic proteins, nuclear proteins, fusion proteins, tagged proteins, chimeric antigen receptor proteins, transcription factors, receptors, receptor binding ligands, viral proteins, proteins comprising cancerous epitopes, antimicrobial proteins, glycoproteins, synthetic proteins, natural proteins, biopolymers, scaffolding proteins, and the like.

In some embodiments, proteins that can be produced using the methods, systems, and platforms described herein include, ELPs (some of them are fused with spytag and spycatcher), RLPs, ligand-binding proteins, pigment proteins, and enzyme (see, e.g., FIGS. 11A-11E and Table 3). In some embodiments, proteins that can be produced using the methods, systems, and platforms described herein include multiple therapeutic biologics, including glucagon-like peptide 1 (GLP-1), that is used to treat type-2 diabetes, and griffithsin, a potent inhibitor of HIV and Zika infections (see, e.g., FIG. 11F).

In addition to genetic circuits, microorganisms described herein can include a means for producing a biomolecule-of-interest, such as a protein/peptide. In accordance with these embodiments, a means for producing a biomolecule-of-interest can include a plasmid comprising a gene that encodes a protein/peptide. In some embodiments, such plasmids include regulatory elements, such as promoters, that control their expression. In other embodiments, such plasmids are inserted into the genome of a microorganism such that its expression can be controlled by adjacent regulatory elements. As described herein, $E.$ $coli$ strain MC4100Z1 included an ePop circuit along with a plasmid expressing BlaM under control of an IPTG-inducible promoter; $E.$ $coli$ strain BL21(DE3) included an ePop circuit and plasmids expressing ELPs-GFP-His or RLPs-GFP-His under control of a T7 promoter; and $E.$ $coli$ strain MC4100Z1 included an ePop circuit and other circuits with T5 promoter regulation (see, e.g., Table 3).

5. ENCAPSULATION MATERIALS

Embodiments of the present disclosure include platforms and systems for biomolecule production using microorganisms that are contained within an encapsulation material (e.g., form microcapsules containing the microorganisms). In accordance with these embodiments, encapsulation materials can be functionally coupled to a genetic circuit within the microorganisms, such that the encapsulation materials are responsive to one or more environmental (e.g., culture) conditions capable of being altered by the microorganisms.

For example, as described herein, microorganism growth can affect both the local pH and ionic strength of culture conditions, which can then cause phase transitions in an encapsulation material (e.g., chitosan network). As microorganisms grew within the microcapsules, the pH and ionic strength of the culture conditions changed, which caused shrinking of the size of the microcapsules, thus releasing a biomolecule-of-interest into the culture media, which can be analyzed/collected/purified. Other means of functionally coupling encapsulation materials to genetic circuit(s) in a microorganism can be based on the various properties of the genetic circuit(s), as would be recognized by one of ordinary skill in the art based on the present disclosure. For example, encapsulating material can be engineered to respond to other culture conditions, such as but not limited to, temperature and light, or any other conditions that microorganisms can be engineered to alter in a manner that can be sensed by the encapsulation material.

As described herein, various encapsulation materials can be used, including but not limited to, any natural and/or synthetic materials capable of forming polymers, such as chitosan, alginate, hyaluronic acid, polyethylene glycol polymers, polyethylene oxide polymers, elastin-like polypeptides (ELPs), resilin-like polypeptides (RLPs), or any derivatives or combinations thereof. Other encapsulation materials can also be used, as would be recognized by one of ordinary skill in the art based on the present disclosure.

Encapsulation materials generally include the capability and properties to form microcapsules in order to contain the microorganisms described herein. In some embodiments, a microcapsule is configured to have a certain size or diameter, for example, to carry out a given function or to mitigate the development of mutant microorganisms. In some embodiments, microcapsules can range from about 50 μm to about 5000 μm in diameter, from about 50 μm to about 4000 μm in diameter, from about 50 μm to about 3000 μm in diameter, from about 50 μm to about 2000 μm in diameter, from about 50 μm to about 1000 μm in diameter, from about 50 μm to about 500 μm in diameter, or from about 50 μm to about 250 μm in diameter. In some embodiments, microcapsules can range from about 100 μm to about 5000 μm in diameter, from about 250 μm to about 4000 μm in diameter, from about 500 μm to about 3000 μm in diameter, from about 500 μm to about 2000 μm in diameter, or from about 1000 μm to about 1500 μm in diameter. In some embodiments, microcapsules can range from about 100 μm to about 500 μm in diameter, from about 200 μm to about 500 μm in diameter, from about 300 μm to about 500 μm in diameter, or from about 300 μm to about 400 μm in diameter. Accordingly, microorganism concentration within microcapsules can range from about $10^2$ to about $10^{10}$, from about $10^2$ to about $10^8$, or from about $10^2$ to about $10^6$, depending on the stain of microorganism, available nutrients, and various culture conditions.

Methods of producing, manufacturing, or fabricating microcapsules containing microorganisms (e.g., MSBs) are generally known in the art, and include, but are not limited to electrospraying, electrohydrodynamic spraying, PDMS stamping, and methods using droplet-generating microfluidic devices, among others.

6. MICROFLUIDICS

Embodiments of the present disclosure also include microfluidics devices and platforms for biomolecule production using microorganisms (e.g., MSBs) as described herein. In accordance with these embodiments, microfluidics devices and platforms can be used to facilitate the production, isolation, collection, purification, and analysis of biomolecules being produced. In some embodiments, microfluidic devices and platforms include an input channel, a production channel, and an assay chamber. The production chamber generally contains the microorganisms contained within the microcapsules, and it can be fluidly coupled to an input channel such that culture media and nutrients flow from a source, into the input channel, and then into the production chamber to reach the microorganisms. More than one input channel can be included, depending on the desired nutrient flow and culture conditions. In some embodiments, the assay chamber is fluidly coupled downstream of the production chamber, in order to facilitate the collection and analysis of a biomolecule-of-interest produced and released by the microorganisms in the production chamber.

In some embodiments, the microfluidics device or platform includes an output channel that is fluidly coupled to the assay chamber or production chamber, such a biomolecule-of-interest produced and released by the microorganisms in the production chamber will flow to the output channel for collection and/or purification. In some embodiments, the microfluidics device or platform includes a purification chip that is fluidly coupled to the assay chamber or production chamber, such a biomolecule-of-interest produced and released by the microorganisms in the production chamber will flow into the purification chip for collection and/or purification. In some embodiments, the purification chip can be modified to facilitate the binding of the biomolecule-of-interest, including coating the inner surface of the purification chip to facilitate binding of the biomolecule-of-interest to a substrate, which can subsequently be treated in order to elute the biomolecule-of-interest (e.g., PEG-coated chelated $Cu^{2+}$).

As described herein, to facilitate isolation, collection, and/or purification of a biomolecule-of-interest from other components, microfluidics devices and platforms of the present disclosure can involve configuring a biomolecule-of-interest to include a tag or other means for attachment or binding to a substrate or to part of the microfluidics device. In conjunction with a particular tag, the microfluidics device can include means for binding the tag such that the biomolecule-of-interest can be separated from other components (e.g., His-tag purification).

7. METHODS OF PROTEIN PRODUCTION

Embodiments of the present disclosure include methods for producing a biomolecule-of-interest using the genetically engineered microorganisms (e.g., MSBs), as described herein. In accordance with these embodiments, the method includes loading a plurality of genetically engineered microorganisms contained in microcapsules into a microfluidics device. The plurality of genetically engineered microorganisms can include a genetic circuit and means for producing a biomolecule-of-interest. The method also includes providing nutrients to the plurality of microorganisms, and allowing for the production of the biomolecule-of-interest. In some embodiments, the method also includes isolating, collecting, purifying, and/or analyzing the biomolecules being produced.

The methods described herein enable the production of a biomolecule-of-interest at various yields. In some embodiments, when the biomolecule-of-interest is a protein/peptide, the yield can be from about 10 mg/L to about 100 mg/L, from about 10 mg/L to about 90 mg/L, from about 10 mg/L to about 80 mg/L, from about 10 mg/L to about 70 mg/L, from about 10 mg/L to about 60 mg/L, from about 10 mg/L to about 50 mg/L, from about 10 mg/L to about 40 mg/L, from about 10 mg/L to about 30 mg/L, or from about 10 mg/L to about 20 mg/L.

As described herein, autonomous biomolecule production can be based on the interaction between a genetic circuit(s) that is functionally coupled to a stimulus-responsive encapsulation material, such as microorganism growth/lysis coupled to pH/ionic strength alterations that cause microcapsules to shrink, thus releasing the biomolecule into the culture. In addition, biomolecule production can be independent of (or decoupled from) microorganism growth/lysis. In some embodiments, biomolecule production may occur, but the biomolecule is actively or passively transported out of the microcapsules without lysis. In some embodiments, genetic circuits may be developed or designed to facilitate growth-independent biomolecule production.

8. MATERIALS AND METHODS

Bacterial Strains. *Escherichia coli* strain MC4100Z1 was used for carrying the ePop circuit alone, or with a plasmid expressing BlaM under control of an IPTG-inducible promoter. *E. coli* strain BL21(DE3) was used for carrying the ePop circuit and plasmids expressing ELPs-GFP-His or RLPs-GFP-His under control of a T7 promoter. *E. coli* strain MC4100Z1 was used for carrying ePop circuit and other circuits with T5 promoter. The constructs used herein are provided in Table 3 below.

TABLE 3

Constructs.

| Construct | Cell strain | Protein Expression Plasmid | Promoter |
|---|---|---|---|
| BlaM | MC4100Z1 | BlaM (Model protein) | pLacI/ara-1 |
| ELPs-GFP-His | BL21(DE3) | (E4-80)-GFP-His (Model protein) (GVGVP)80 | T7 |
| RLPs-GFP-His | BL21(DE3) | (RLP-1)-GFP-His (Model protein) (GRGDSPYQ)20 | T7 |
| RLP-2-GFP-His | MC4100Z1 | (RLP-2)-GFP-His (GRGDQPYQ)20 | T5 |
| RLP-3-GFP-His | MC4100Z1 | (RLP-3)-GFP-His (GRGDSPYS)80 | T5 |
| pAAA | MC4100Z1 | His-SpyTag-Elastin-SpyTag-Elastin-SpyTag | T5 |
| pBBB | MC4100Z1 | His-SpyCatcher-Elastin-SpyCatcher-Elastin-SpyCatcher | T5 |
| pAA-mcherry | MC4100Z1 | His-SpyTag-Elastin-mCherry-Elastin-SpyTag | T5 |
| pBB | MC4100Z1 | His-SpyCatcher-Elastin-RGD-Elastin-SpyCatcher | T5 |
| GLP-1 | BL21(DE3) | GLP-1-ELP4-80-His (GVGVP)80 (Therapeutic) | T7 |
| Griffithsin | BL21(DE3) | Griffithsin-His (Therapeutic) | T7 |
| SUP | MC4100Z1 | His-SpyTag-Elastin-SpyTag-Elastin-SpyTag-SUP | T5 |
| 3A-BlaM | MC4100Z1 | His-SpyTag-Elastin-SpyTag-Elastin-SpyTag-BlaM | T5 |
| 3A-PrancerPurple | MC4100Z1 | His-SpyTag-Elastin-SpyTag-Elastin-SpyTag-PrancerPurple | T5 |

*Unless otherwise indicated, each construct includes p15A replication origin and is co-expressed with ePop circuit.

Circuit and Plasmids. ePop (ColE1 origin) was published previously. Briefly, it was constructed using the luxbox region (140 bp upstream of luxI in *V. fischeri*) from pluxGFPuv and E gene coding sequence from φX174 (NEB). Each region was PCR-amplified and then joined together in an overlap PCR reaction. The 'lux box-E gene' fragment was inserted into the AatII site of host vector pLuxRI2.

BlaM (p15A origin) was published previously. Briefly, it was constructed by PCR-amplifying bla gene from pSND-1 without first 66 base pairs and inserting it under Plac/ara-1 of pPROLar.A122 (Clonetech).

ELPs-GFP-His (model protein), RLPs-GFP-His, GLP-1-ELPs-His and other ELPs/RLPs variants, were previously constructed. The fragments were cloned into the vector with T7 or T5 promoter and p15A origin.

His-AAA, His-BBB, His-AA-mcherry and His-BB were constructed using plasmids previously described. The fragments were cloned into the vector with T5 promoter and p15A origin.

3A-SUP was constructed using plasmids previously described. The fragment was cloned into the vector with T5 promoter and p15A origin.

3A-PrancerPurple was constructed using a plasmid from ATUM (CPB-37-441) and His-AAA. The PrancerPurple was cloned into the downstream of His-AAA.

3A-BlaM was constructed using the synthesized fragment (3A-BlaM) from GENEWIZ. The fragment was cloned into the vector with T5 promoter and p15A origin.

Griffithsin-His was constructed using plasmids previously described. The fragment was cloned into the vector with T7 promoter and p15A origin.

Growth Media. The LB medium: 25 g LB Broth Powder (MO BIO Laboratories, Inc) was added into 1 L deionized H2O. After autoclaving for 45 mins, the LB medium was stored at room temperature. The medium was supplemented with appropriate antibiotics (100 µg/mL chloramphenicol, 50 µg/mL kanamycin, 100 µg/mL ampicillin) when applicable.

The M9 medium: 1×M9 salts (48 mM Na2HPO4, 22 mM KH2PO4, 862 mM NaCl, 19 mM NH4Cl), 0.4% glucose, 0.2% casamino acids (Teknova), 0.5% thiamine (Sigma), 2 mM MgSO4, 0.1 mM CaCl2 were added into 1 L deionized H2O. M9 medium was adjusted with to pH=7 by VWR Symphony SB70P pH Meter and filtrated through 0.22 µm filter.

Liquid Cultures. Cells carrying the ePop circuit were streaked onto an agar plate supplemented with 2% (w/v) glucose, and incubated at 37° C. for 16 h. Then, a single colony was picked and inoculated in 3 mL LB medium. The agar and the liquid culture medium were supplemented with appropriate antibiotics when applicable. For cells carrying ePop circuit, 2% (w/v) glucose was supplemented in the overnight cultures. Bacteria carrying all protein-expression circuits were induced with 1 mM IPTG.

Evaluation of Programmed Lysis. Engineered bacteria carrying the ePop circuit (MC4100Z1(ePop)) were inoculated in 3 mL LB medium containing antibiotics and 2% glucose, and cultured at 37° C. with a shaking speed at 250 rpm for overnight. Then the calibrated cultures were diluted into LB medium, which was supplemented with antibiotics and various concentration of glucose. 200 µL cultures were aliquoted into 96-well plates, which were then sealed with 50 µL mineral oil to prevent evaporation. Optical density of cultures (OD600) was measured using a plate reader (Tecan infinite M200 pro). For data analysis, the measured OD600 values were background corrected. Lysis circuit is considered functional when multiple cycles of population oscillations can be observed during long-term batch cultures.

For observing the oscillatory behavior of cells on the microfluidic device, the 20 µL overnight culture (MC4100Z1(ePop/GFP)) was inoculated into 2 mL LB medium and cultured for 8 hours. Then, the cells were re-suspended in M9 medium and loaded them into the culturing chamber. M9 medium was supplemented continuously at 120 µL/hour. The design of the microfluidic device was published previously, while with the height of device is about 1.5 µm. The whole device was cultured at 37° C., and Nikon Ti-E microscope with 100× objective was employed for the long-term monitoring.

Figures 14A, 14B, 14C:
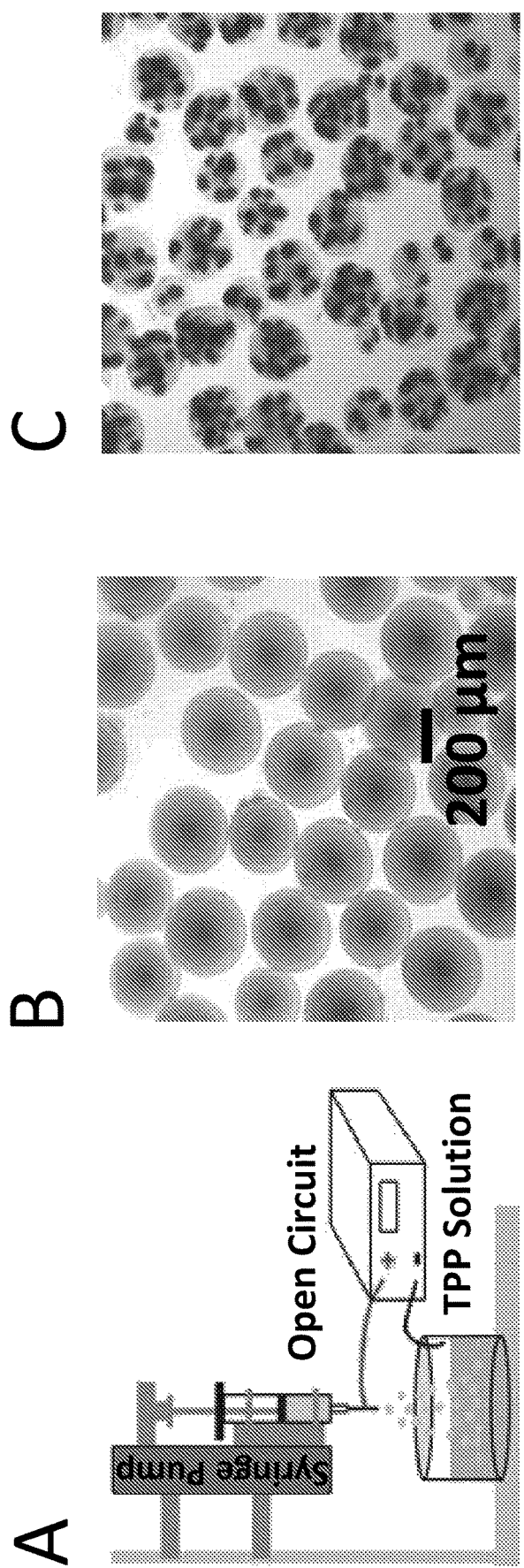
FIGS. 14A-14C include representative results demonstrating the encapsulation of bacteria in chitosan microcapsules by electrospray methods.

Production of Alginate and Chitosan Microcapsules. Chitosan microcapsules containing bacterial cells were fabricated by electrospray (FIG. 14). A homogeneous mixture of 2% (w/v in 1% acetic acid solution) chitosan (Sigma-Aldrich) solution and cells was transferred into a syringe with an attached blunt tip. The syringe was placed in an electrospray system equipped with a syringe pump. The anode of the electrospray system was connected to the needle and the cathode was connected to a sterile metal receiving container with crosslinking solution (5% w/v tripolyphosphate). The solution was sprayed at high voltage (5 kV) to the receiving container with stirring. The microcapsules were collected by centrifugation at 500 g for 5 minutes and washed twice using PBS. The procedure and equipment of preparing alginate capsules was the same as described herein. Instead, 2% (w/v in D.I. water) sodium alginate (Sigma-Aldrich) solution was used, and crosslinking solution is 1.5% (w/v) calcium chloride.

Efficiency of Protein Export. A high molecular weight (about 70000 g/mol) dextran conjugated with Rhodamine (Sigma-Aldrich) was used as a model protein. About 30 µL dextran-Rhodamine (20 mg/mL) and 30 µL overnight culture of MG1655 cells (sensitive to Ampicillin) were mixed and encapsulated them using 300 µL chitosan or alginate solutions. The chitosan/alginate capsules were first washed three times by PBS/CaCl2 (1.5% w/v), and then cultured in 3 mL LB or M9 medium. As a control, the capsules were cultured in LB or M9 medium with ampicillin eliminating the cell growth. 100 µL of the culturing medium was taken at different time points and the fluorescence signal from medium was measured by a plate reader (Tecan infinite M200 pro). Measurements were done in triplicate and background corrected.

Quantifying Beta-lactamase Activity. Bacteria MC4100Z1 carrying the ePop circuit and a BlaM-expressing plasmid (MC4100Z1 (ePop/BlaM)) were induced with 1 mM IPTG. About 20 µL supernatant was diluted into 200 µL using PBS and mixed with Fluorocillin™ Green (Thermo Fisher) to attain a final substrate concentration of 2 µM. Upon cleavage by BlaM, Fluorocillin™ Green reagent can be converted to a fluorescent product. The resulting fluorescence was measured using a plate reader (Tecan infinite M200 pro). Measurements were done in triplicate and background corrected.

Genetic Stability. Kinetic models were developed to examine the genetic stability of the ePop circuit under different conditions, and the impact on the overall efficiency of protein production. Table 4 and Table 5 (below) provide details pertaining to model development, parameter choices, and initial condition for simulation.

TABLE 4

Definitions and parameter values used in ODE modeling.

| Parameter | Definition | Value |
|---|---|---|
| $\alpha_1$ | Maximum growth rate(1/hr) | 1 |
| $\alpha_2$ | Intrinsic mutant generation frequency | 0.1 |
| $\alpha_3$ | Nutrient consumption rate (nmoles/cell) | 0.1 |
| $\beta_1$ | Constitutive synthesis rate of POI (nmoles/cell) | 1 |
| $\beta_2$ | Recovery rate of nutrients (nmoles/cell) | $0.1\alpha_3$ |
| $\beta_3$ | Synthesis rate of E protein (nmoles/(cell × hr)) | 5 |
| $\gamma_1$ | Intrinsic death rate of mutants (1/hr) | 0 |
| $\gamma_2$ | Intrinsic degradation rate of E (1/hr) | 0.5 |

TABLE 4-continued

Definitions and parameter values used in ODE modeling.

| Parameter | Definition | Value |
| --- | --- | --- |
| $\gamma 3$ | Maximum lysis rate (1/hr) | $2\alpha 1$ |
| k1 | Half-maximal threshold for growth by nutrients (µM) | 0.01 |
| k2 | Half-maximal threshold for E protein lysis (µM) | 1 |
| r | Weighing factor | 0.5 |
| p | Hill coefficient for lysis | 3 |
| Nm | Carrying capacity of population (cells/mL) | 1 |
| Vr | Volume ratio | 0.01 |
| Vl | Conversion factor (mL) | 105 |
| fN | Transport rate constant(1/hr) | 10-6 |
| fS | Transport rate constant(1/hr) | 1 |
| fP | Transport rate constant(1/hr) | 0.5 |
| fM | Transport rate constant(1/hr) | 10-6 |
| D | Dilution ratio | 1 |

TABLE 5

Initial conditions used in ODE modeling.

| one-compartment | [N; S; E; P; M] | [10-2; 102; 0; 0; 0;] |
| --- | --- | --- |
| two-compartment | [N1; S1; E1; P1; M1] in MSB | [10-4; 0.5; 0; 0; 0] |
|  | [N2; S2; E2; P2; M2] outside MSB | [0; 0.5; 0; 0; 0;] |

Figures 8A, 8B:
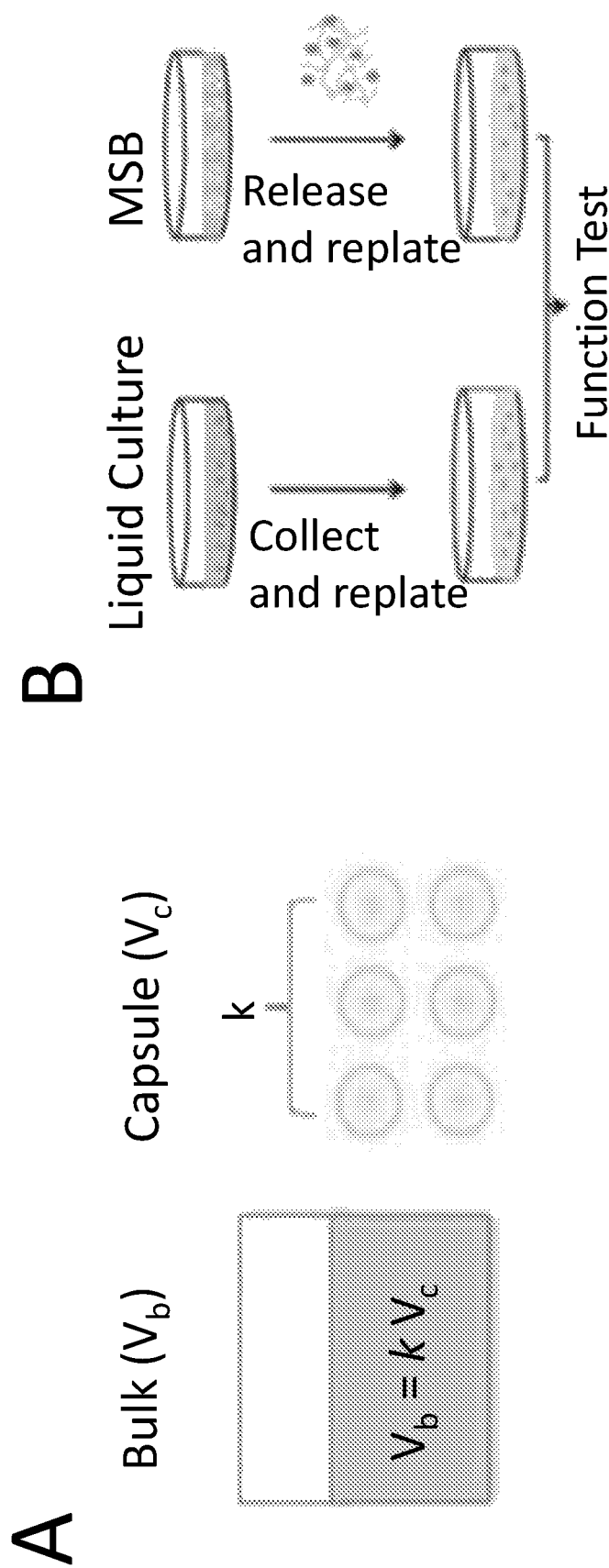
FIGS. 8A-8D include representative schematics (FIGS. 8A and 8B) and graphs (FIGS. 8C and 8D) demonstrating microencapsulation-mediated enhancement of circuit stability.
Figures 8C, 8D:
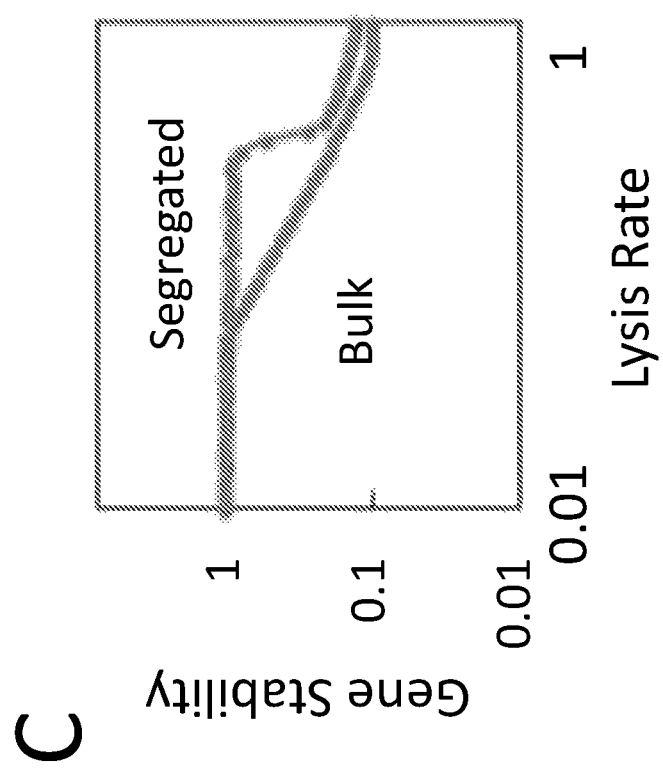

To determine the dependence of gene stability on time experimentally, 30 µL overnight culture of MC4100Z1 (ePop) cells was inoculated into 3 mL M9 medium, or encapsulated into capsules using 300 µL chitosan solution, and supplemented with additional 3 mL M9 medium. After 24, 48 and 72 hours, bacteria were collected from the bulk culture or from MSBs (see detailed releasing procedure below) and plated onto agar plates. To release bacteria from MSBs, 2.5 M NaCl was used to destabilize the capsules by repeated pipetting (FIG. 8C). From each plate, 10 clones were picked and tested whether the ePop circuit dynamics were maintained for each clone. If the circuit function was maintained, the clone is considered to be phenotypically equivalent to a wild type. The percentage of clones maintaining the circuit function was used to generate FIG. 3D Measurements were done in triplicate.

Figures 7A, 7B:
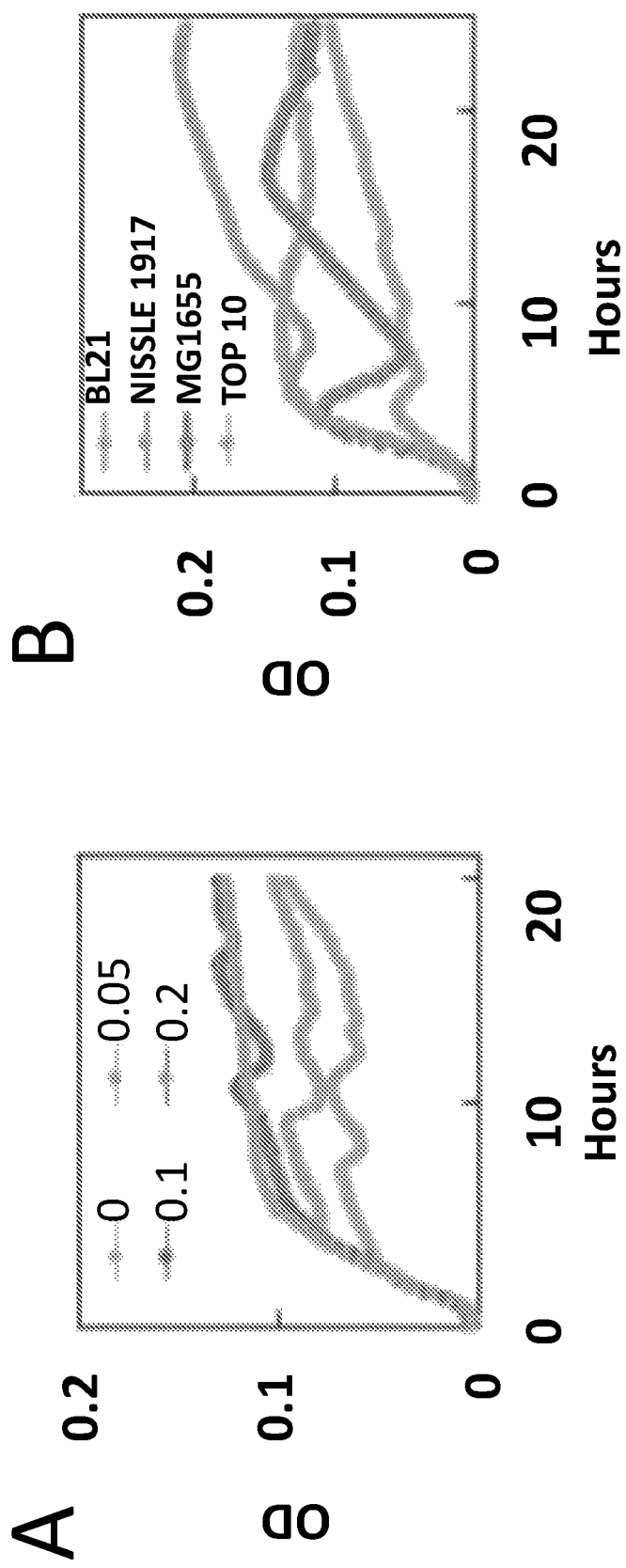
FIGS. 7A-7D include representative results characterizing the different modules of the MSB platforms of the present disclosure.

To determine the dependence of the circuit stability on the lysis rate, 30 µL overnight culture of MC4100Z1 (ePop) cells was inoculated into 3 mL M9 medium, or encapsulated into capsules using 300 µL chitosan solution, and supplemented with the 3 mL M9 medium. Each culture was supplemented with 0%, 0.05% or 0.1% (w/v) glucose to adjust lysis rate, which decreases with the glucose concentration (FIG. 7B). After 72 hours, the cells were collected from the bulk culture or from the MSB culture and plated onto agar plates. From each plate, 10 clones were picked and tested for whether the ePop circuit dynamics were maintained for each clone. The percentage of clones maintaining the circuit function was used to generate FIG. 3E Measurements were done in triplicate.

Beta-lactamase Activity. Equal amount (30 µL) of overnight culture of MC4100Z1(ePop/BlaM) cells were inoculated into 3 mL M9 medium, or encapsulated into capsules using 300 µL chitosan solution, and supplemented with 3 mL M9 medium. After cultured for 72 hours at 37° C. in an incubator, 20 µL supernatant was diluted into 200 µL using PBS and mixed with Fluorocillin™ Green (Thermal fishier technology) to attain a final substrate concentration of 2 µM. The resulting fluorescence was measured using a plate reader (Tecan infinite M200 pro) as a function of time. Each measurement was done in triplicate and background corrected.

The conversion of the Fluorocillin into a fluorescent product can be described by the Michaelis-Menten kinetics:

$$v = \lim_{t \to 0} \frac{dF}{dt} = \frac{kE_0[S]}{K + [S]},$$

where v is the initial rate of increase in the fluorescence (F), k is the catalytic constant, K is the Michaelis-Menten constant, $E_0$ is the concentration of BlaM, and [S] is the concentration of the substrate (Fluorocillin). When the substrate is saturating ([S]>>K), $v=kE_0$, thus v provides a direct measurement of the enzyme activity. Experimentally, v is determined by taking the time derivative of F in the initial time window, when F increases linearly with time (FIG. 9).

Microfluidic Device Fabrication. The photoresist master mold was fabricated by spin-coating two layers of SU8 3050 (MicroChem, 1000 rpm for 30 seconds) onto a silicon wafer, which was then pre-baked for 60 mins at 95° C., and UV crosslinked with a pre-designed photomask (AutoCAD). The UV exposed wafer was post-baked for 20 mins at 95° C., developed with SU8 developer, and finally hard-baked for overnight at 95° C. The height of the SU8 mold for the microfluidic device was about 450 µm. Next, the PDMS microfluidic device containing the designed structure was fabricated by pouring a mixed PDMS solution (Dow Corning SYLGARD® 184, 10:1 as monomer: curing agent) onto the master mold, degassing the solution under vacuum, and baking it at 80° C. for 30 mins. After the solution solidified, holes were drilled for input and output flow with tissue punches. The PDMS device was bonded to a cover slip by plasma treatment at 40 watts for 30 seconds.

Two different microfluidic devices were fabricated, depending on its purpose. The first device was designed to monitor and quantify BlaM production. The device includes a main channel (width=500 µm, length=5.3 mm), a circular culturing chamber (diameter=1 mm), two trapping channels (width=60 µm, length=720 µm), a substrate delivery channel (width=150 µm, length=2.2 mm), an assay chamber (Diameter=400 µm), and an output channel (width=240 µm, length=2.2 mm). The capsules were captured in the culturing chamber since their diameters (200-400 µm) were larger than that of the trapping channel. The substrate delivery channel was used to flow in a fluorocillin solution to assay the activity of BlaM released from the culturing chamber.

The second device was designed to demonstrate integrated protein production and purification. It includes two separate chips. The first, a production chip is similar to that described above for the first device. The production chip includes a main channel (width=1200 µm, length=8 mm), a culturing chamber (diameter=3 mm), and three trapping channels (width=90 µm, length=4.5 mm). The three trapping channels merge into a single output, connected, by a Teflon tube, to the second chip (a purification chip). The purification chip includes repetitive serpentine channels (width=1 mm, length=17 mm, diameter out=1.75 mm, diameter in=0.75 mm). The PDMS device was glued to a Cu-NTA (copper-nitrilotriacetic acid) coated glass-slide (MicroSurfaces Inc) for binding His-tagged proteins.

Culturing and Monitoring MSBs. Before loading microcapsules into the culturing chamber, the microfluidic device was vacuumed for 15 mins to prevent generation of air bubbles. Unless indicated otherwise, a programmable syringe pump (Harvard Apparatus, Pump 11 Elite) was used to control the input flow patterns. For periodic pulsing, the flow rate of each perfusion was set as 0.5 μL/min for 30 mins and then delayed (0 μL/min) 90 mins before the next pulse. The flow pattern for nutrients and substrate (10 μM Fluorocillin in PBS) is synchronized. For binding of the crude into the purification chip, the flow rate was set as 0.5 μL/min. The same flow rate was used for subsequent washing (PBS) and elution steps (100 mM EDTA). The microfluidic device was installed in the microscopy hood and cultured at 37° C. An inverted fluorescence microscope (Nikon Eclipse Ti) with 10× objective was employed to monitor the dynamics of capsule size and the fluorescence signal generated by the enzymatic reactions. The fluorescence signal intensity was quantified by averaging the gray level of whole assay chamber using ImageJ.

Protein Purification. For His-tag affinity purification, cOmplete™ His-Tag Purification Column (Sigma-Aldrich) was used for on-bench continuous purification using the protocol suggested by Sigma-Aldrich. cOmplete™ His-Tag Purification Column was used due to its minimized nickel ion leakage, which can be important for therapeutic related protein purification.

For purification of ELPs-tagged proteins by microfiltration, 10 mL crude from a MSB culture was first filtrated with a 0.45 μm HT Tuffryn® Membrane and then mixed with the exogenous ELPs (5 μM) and NaCl (2 M) to trigger the LCST phase transition. The mixture containing the aggregates (consisting of the trigger ELPs and ELPs-tagged target protein) was loaded and filtrated through a syringe coupled with a 0.2 μm HT Tuffryn® Membrane. To wash the aggregates deposited onto the filter, 5 mL of 2 M NaCl was injected through the filter to remove proteins in the solution while retaining the aggregates. To elute the aggregation, 1 ml of D.I. water was passed through the filter, causing re-solubilization of the retained aggregates. The eluted solution was collected for the next step His-tag purification. For all protein samples, SDS-PAGE, using Coomassie Blue stain, was used to verify the purity of the protein-of-interest.

Production of ELPs/RLPs tagged proteins, therapeutic proteins, and other proteins using MSB. For on bench production of ELPs/RLPs tagged, therapeutic and other proteins, 375 μL of overnight culture of cells carrying both the lysis circuit and protein expression circuit were centrifuged and re-suspended in 37.5 μL LB medium, and encapsulated into 375 μL chitosan solution for the MSB culture. The capsules were loaded into 20 mL syringe supplemented with 10 mL LB medium with appropriate antibiotics, and cultured in 37° C. for 24 hours. A 0.45 μm HT Tuffryn® Membrane with low protein binding property was attached at the tip of the syringe to avoid leaking and evaporation of the culture medium. The concentration of purified protein was measured by absorbance of 280 nm by using Nanodrop Spectrophotometer ND-1000.

Long term monitoring of MSB platform performance. To evaluate long-term performance of MSBs, the MSB was first made using the same protocol described above. Briefly, 375 μL of overnight culture of cells BL21(DE3) (ePop/ELPs-GFP-His) were centrifuged and re-suspended in 37.5 μL LB medium, and encapsulated into 375 μL chitosan solution for the MSB culture. The MSB was centrifuge at 7000 rpm for 5 mins and then stored at either 4° C. or −80° C. After various time windows, the MSB was taken out and then recovered with 3 mL LB medium and cultured at 37° C. for 48 hours. The amount of purified protein was quantified by measuring absorbance at 280 nm. All the data is normalized with the amount of protein produced using MSBs made fresh and cultured with 3 mL LB at 37° C. for 48 hours. The experiments are done in triplicate.

Modification on the surface of the capsules by layer-by-layer coating technique. About 375 μL of overnight culture of cells (MC4100Z1 (ePop/BlaM)) were centrifuged and re-suspended in 37.5 μL LB medium, and encapsulated into 375 μL chitosan solution. The capsules were washed first with PBS, and then incubated in 1.5 mL alginate solution (0.1%/(w/v)) for 15 mins with gentle shaking. The resultant capsules were centrifuged, collected, washed again with PBS and then incubated in 1.5 mL chitosan solution (0.4%/(w/v)) with gentle shaking for another 15 mins. The resultant capsules were washed again with PBS and collected.

To calculate the percentage of escape cells and compare the yield, equal amount of normal and surface modified capsules were inoculated into 3 mL LB with appropriate antibiosis and 1 mM IPTG, and cultured in 37° C. for 24 hours. To calculate the percentage of escape cells, the CFU in the surrounding medium is counted for both cases (normal and modified) in MSB culture, and divided by the CFU of bulk culture condition. To compare the yield, 20 μL supernatant was diluted into 200 μL using PBS and mixed with Fluorocillin™ Green (Thermo Fisher) to attain a final substrate concentration of 2 μM. Upon cleavage by BlaM, Fluorocillin™ Green reagent can be converted to a fluorescent product. The resulting fluorescence was measured using a plate reader (Tecan infinite M200 pro). Measurements were done in triplicate and background corrected.

Mathematical Derivation. The population is defined as N, which stands for the density of the population. The unit for the density is defined as cells·mL$^{-1}$. Here, the total number of population would be N·V, where V is the volume of the culturing environment. Because spatial segregation by encapsulation provides smaller volume for each population, the total number of cells $N_t$ for each swarmbot capsule would be smaller than that of the bulk liquid culturing environment. The scale for the total cell number is assumed as below.

MSB capsule: $N_t \in [0, 10^3]$

Liquid culture: $N_t \in [0, 10^9]$

Then, how segregation increases the genetic stability against rise in number of mutants can be mathematically derived. First, $\lambda$ is the average number of mutants in a population calculated by frequency of mutants, $\rho$, and the change in density defined with growth rate, G, cell density, N, and volume, V.

$$\lambda = \rho V G N \Delta t$$

Following the equation for Poisson distribution, we can derive the following. Probability of no mutants with Poisson distribution:

$$P(k) = \frac{\lambda^k e^{-\lambda}}{k!}$$

$$P(O) = e^{-\lambda} = e^{-\rho V G N \Delta t} = (e^{-\rho \Delta N})^V$$

Probability of no mutants for MSB capsule (The subscript S stands for small volume).

Defining.

$$P(O)_s = \sum_k \alpha^{V_S} = k\alpha^{V_S}, \text{ where } e^{-\rho \Delta N} = \alpha$$

Probability of no mutants for bulk liquid culture (The subscript L stands for large volume).

$$P(O)_L = \alpha^{V_L} = \alpha^{V_s k} \text{ where } V_L = V_s k$$

Thus, the benefit of MSB platform defined as η can be written as $$\eta = \frac{P(O)_s}{P(O)_L} = \frac{k\alpha^{V_s}}{\alpha^{V_s k}} = \frac{k\alpha^{V_s}}{(\alpha^{V_s})^k}$$

where $$0 < \alpha^{V_s} < 1$$

Defining $$m = \alpha^{V_s}$$

Then $$\eta(m) = \frac{k\alpha^{V_s}}{(\alpha^{V_s})^k} = \frac{km}{m^k}$$

The derivative of η(m)

$$\eta'(m) = \frac{(m-k^2)m^{k-1}}{(m^k)^2}$$

With $$k \geq 1, m < 1$$

$$\eta' = \frac{(m-k^2)m^{k-1}}{(m^k)^2} < 0$$

The function is monotonic decaying.

$$\eta(1) = 1$$

Therefore, $$\eta(m) > 1$$

Especially, the benefit increases with the degree of segregation degree increases (m increases).

Model equations and justifications. A kinetic model was developed to examine how spatial segregation (via encapsulation of bacteria in microcapsules) modulates the genetic stability of the ePop circuit and the yield of a protein-of-interest. The model comprises a set of algebraic equations and ordinary differential equations that describe the temporal dynamics of five components: wild-type cell density (N), nutrient concentration (S), E protein (E), protein-of-interest (P) and mutant density (M).

Model equations for one compartment (e.g., the bulk culture). Growth rate (G) is modeled by the Monod equation that accounts for availability of nutrients. Also, it includes a logistic term that accounts for the carrying capacity of the system. The carrying capacity can be modulated depending on the environment (MSB versus culturing chamber):

$$G = \frac{\alpha_1 S}{k_1 + S}\left(1 - \frac{N+M}{N_m}\right)$$

Lysis rate (L) is modeled as depending on the E protein concentration following a Hill function, with a Hill exponent (p):

$$L = \frac{\gamma_3 E^p}{k_2^p + E^p}$$

Cell density changes with respect to growth and lysis rates. Decrease in density due to mutant generation is assumed to be negligible:

$$\frac{dN}{dt} = GN - LN$$

Nutrient level changes by consumption or recovery from cells upon lysis:

$$\frac{dS}{dt} = -\alpha_3 G(N+M) + \beta_2(LN + \gamma_1 M)$$

The rate of E protein synthesis is assumed to be proportional to the cell density. The degradation of E protein is assumed to follow a first-order kinetics. The effective degradation rate constant accounts for a basal rate constant γ2 and dilution due to cell growth. A weighing factor r, modulates the decay rate of E protein:

$$\frac{dE}{dt} = \beta_3 N - r(\gamma_2 + G)E$$

The rate of release of a protein-of-interest (POI) into the environment is proportional to the lysis rate (for simplicity, it was assumed that mutant cells do not lyse or contribute to the production of the POI):

$$\frac{dP}{dt} = \beta_1(LN + \gamma_1 M)$$

After generation (see below), the mutant population is assumed to grow following the same dynamics as the wild type but do not undergo lysis:

$$\frac{dM}{dt} = GM - \gamma_1 M$$

Generation of a mutant cell is implemented by the following logic. First, it was assumed that the average number of potential mutants arising from a population is proportional to the increase in cell density for a certain time window (i.e., mutants only arise if there is active cell growth): $\lambda = \alpha_2 GNV_l \Delta t$, where $V_l$ is a conversion factor to convert density N into total number of cells in the specified environment. Whether a mutant actually arises is assumed to follow a Poisson distribution, where the probability of no mutant is $P(O) = e^{-\lambda}$. That is, the probability of maintaining mutant-free decreases exponentially with λ, which increases with the population size, the effective growth rate, and the time window of interest (Δt).

In a numerical simulation, this scenario described above is implemented by generating a random number between 0 and 1 during each time step. If the random number is <P(O), a mutant is added in the simulation with conversion factor of $V_f$. This conversion factor is used to convert the number of mutants into cell density. This number sets the initial condition for the mutant population thereafter. Mutant generation is assumed to occur only once.

Two compartment model for the MSB dynamics. The equations are expanded and applied to describe the dynamics in two compartments, by accounting for transport between the compartments.

$$G_1 = \frac{\alpha_1 S_1}{k_1 + S_1}\left(1 - \frac{N_1 + M_1}{N_m}\right)$$

$$L_1 = \frac{\gamma_3 E_1^p}{k_2^p + E_1^p}$$

$$G_2 = \frac{\alpha_1 S_2}{k_1 + S_2}\left(1 - \frac{N_2 + M_2}{N_m}\right)$$

$$L_2 = \frac{\gamma_2 E_2^p}{k_2^p + E_2^p}$$

Inside the MSB (index=1).

$$\frac{dN_1}{dt} = |G_1 N_1 - L_1 N_1 - f_N N_1$$

$$\frac{dS_1}{dt} = -\alpha_3 G_1(N_1 + M_1) + \beta_2(L_1 N_1 + \gamma_1 M_1) + f_S(S_2 - S_1)$$

$$\frac{dE_1}{dt} = \beta_3 N_1 - r(\gamma_2 + G_1)E_1$$

$$\frac{dP_1}{dt} = \beta_1(L_1 N_1 + \gamma_1 M_1) + f_P(P_2 - P_1)$$

$$\frac{dM_1}{dt} = G_1 M_1 - \gamma_1 M_1 - f_M M_1$$

Outside the MSB (index=2).

$$\frac{dN_2}{dt} = G_2 N_2 - L_2 N_2 + f_N V_r N_1 - DP(t)N_2$$

$$\frac{dS_2}{dt} = -\alpha_3 G_2(N_2 + M_2) + \beta_2(L_2 N_2 + \gamma_1 M_2) - f_S V_r(S_2 - S_1) + DP(t)(I_S - S_2)$$

$$\frac{dE_2}{dt} = \beta_3 N_2 - r(\gamma_2 + G_2)E_2$$

$$\frac{dP_2}{dt} = \beta_1(L_2 N_2 + \gamma_1 M_2) - f_P V_r(P_2 - P_1) - DP(|t)P_2$$

$$\frac{dM_2}{dt} = G_2 M_2 - \gamma_1 M_2 - f_M V_r(M_2 - M_1) - DP(t)M_2$$

A unidirectional transport of cells from MSB capsule to the environment was assumed. The equations are developed for simulating both static and periodic dosing of fresh medium into the MSB platform assuming a microfluidic set-up. Is indicates concentration of nutrients in the fresh media. P(t) is a function of pulse duration, and period.

9. EXAMPLES

It will be readily apparent to those skilled in the art that other suitable modifications and adaptations of the methods of the present disclosure described herein are readily applicable and appreciable, and may be made using suitable equivalents without departing from the scope of the present disclosure or the aspects and embodiments disclosed herein. Having now described the present disclosure in detail, the same will be more clearly understood by reference to the following examples, which are merely intended only to illustrate some aspects and embodiments of the disclosure, and should not be viewed as limiting to the scope of the disclosure. The disclosures of all journal references, U.S. patents, and publications referred to herein are hereby incorporated by reference in their entireties.

The present disclosure has multiple aspects, illustrated by the following non-limiting examples.

Example 1

Assembly of the MSB Platform by Cell-Material Feedback

Figures 2A, 2B:
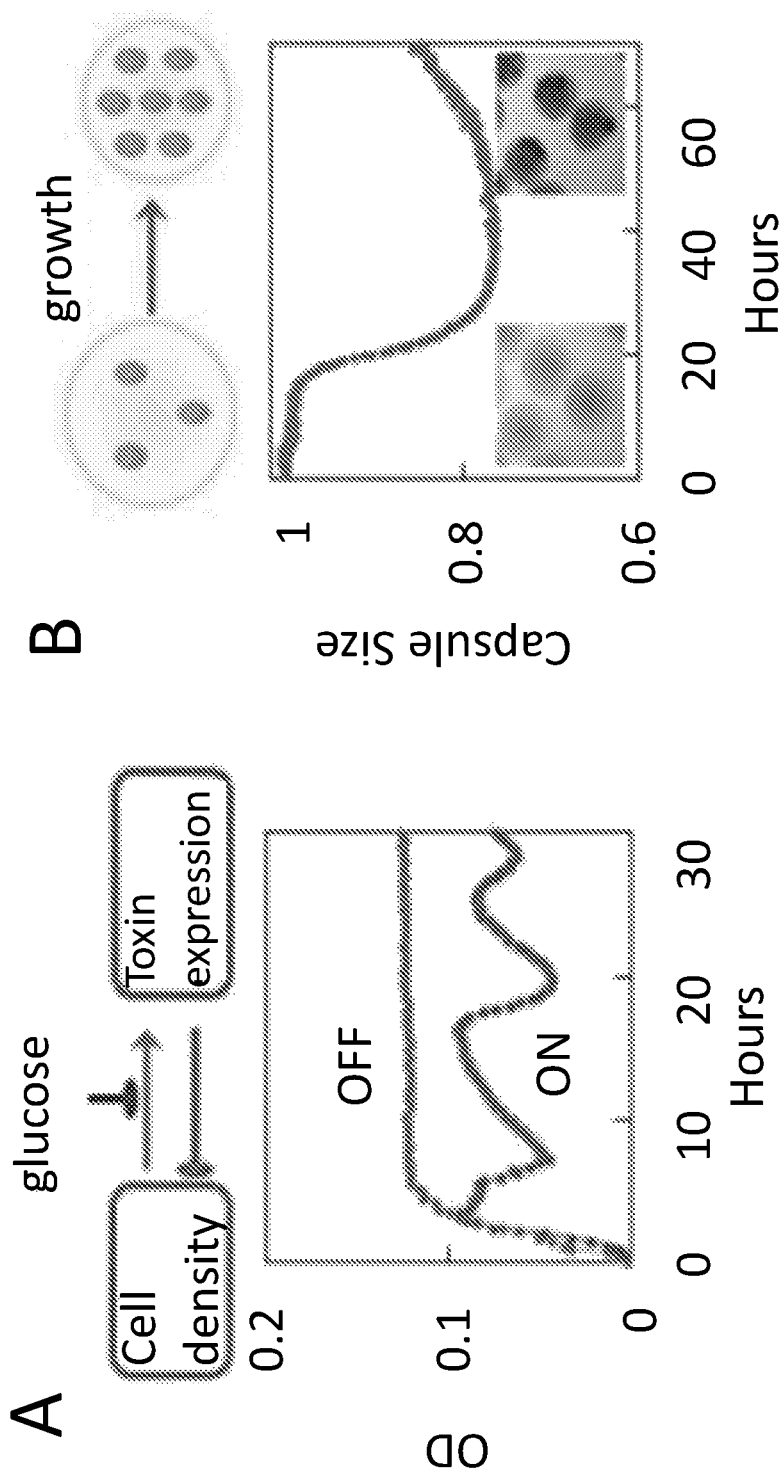
FIGS. 2A-2C include representative results of the basic functions of the modules of MSBs.

Two basic modules, autonomous lysis cells and growth sensitive capsules, can be used to integrate function of the systems of the present disclosure, as shown in FIGS. 1A-1D. In accordance with these embodiments, engineered ePop circuit was used to program autonomous lysis. The circuit exploits the cell-density dependent copy number control in ColE1-type plasmids that is coupled to leaky expression of a toxin (FIG. 2A). High cell densities led to an increased plasmid copy number and greater E protein expression, which then led to lysis of a subpopulation of the bacteria (FIG. 2A). The circuit dynamics are readily tunable by exogenously controlling the glucose level (FIG. 7A) or using different *E. coli* strains, including a probiotic strain (FIG. 7B).

The polysaccharide chitosan was used as the encapsulating material due to its biocompatibility and stimulus responsiveness. The resulting three-dimensional cross-linked networks inside the polymeric capsules trapped the living cells and large debris but allowed transport of small molecules and proteins. At low pH, protonation of the amine groups extends the chitosan chains due to electrostatic repulsion between the charged groups, therefore swelling the network. In contrast, a high ionic strength shields the electric charges, leading to shrinking of the network due to collapse of the polymer chains.

Bacterial growth affected both the local pH and ionic strength, which can then cause phase transition in the chitosan network. Therefore, the change in size of the capsule can both influence and provide a visual readout for the dynamics of encapsulated bacterial. Indeed, when the engineered bacteria (MC4100Z1 (ePop/GFP)) encapsulated capsules were cultured in M9 medium, their growth led to shrinking of the chitosan network (FIG. 2B). In LB medium, the capsules swelled slightly before shrinking as the encapsulated bacteria grew.

Figure 2C:
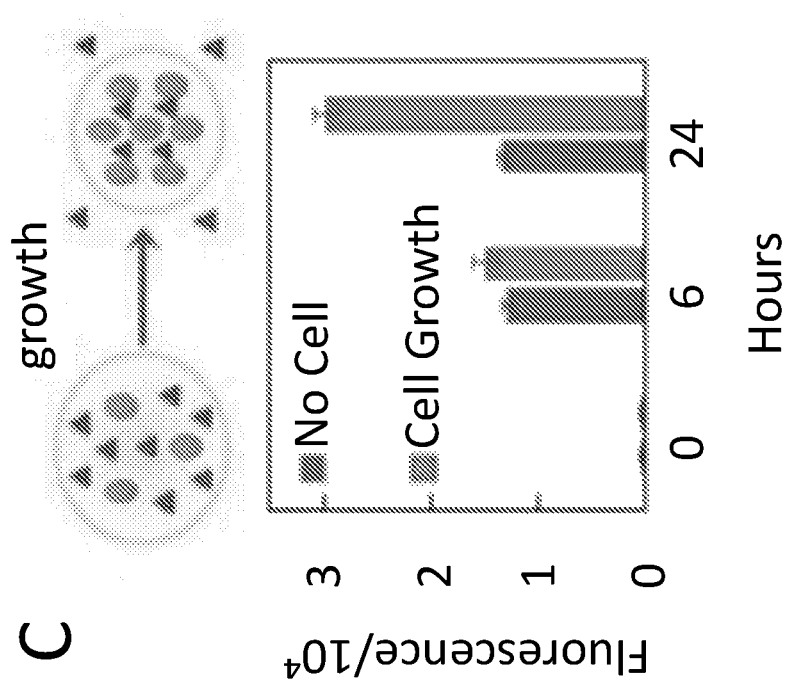
Figure 7C:
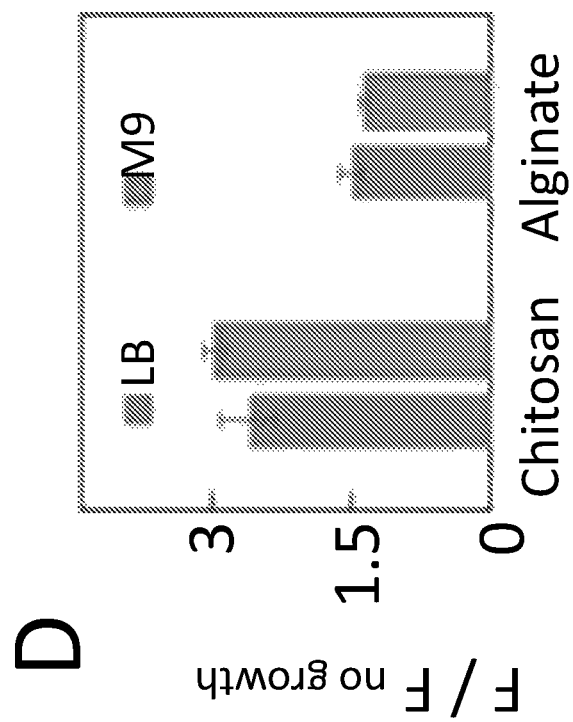
Figure 7D:
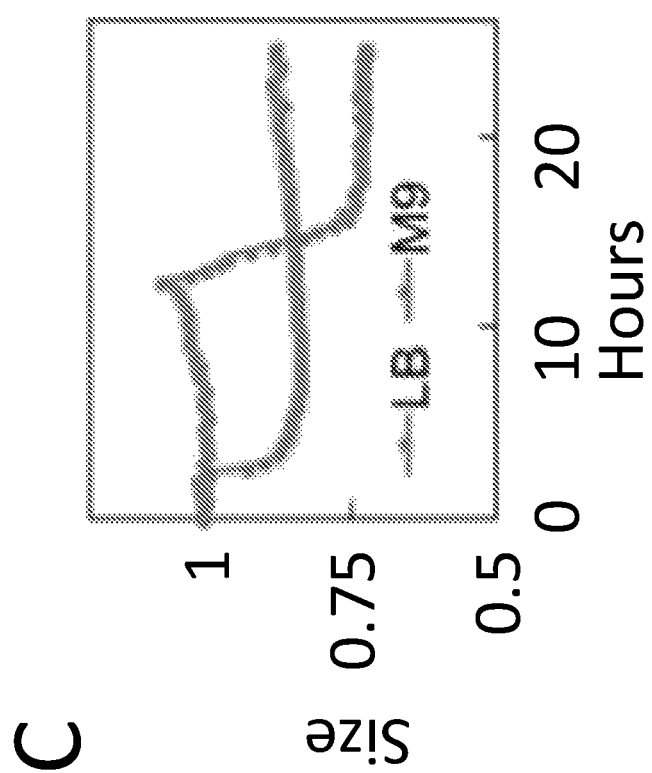

The phase transition of chitosan capsule is a general property of the changed microenvironment due to bacterial growth with or without the ePop circuit (FIG. 7C). For the encapsulated ePop bacteria, the transition is temporally correlated with the circuit-mediated lysis, which occurs at a sufficiently high local cell density. The capsule collapse driven by bacterial growth enhanced export of an encapsulated fluorescent macromolecule (FIG. 2C) by about 2.25-fold (M9 medium) in comparison to the control, where the macromolecule was encapsulated with cells but do not grow. The enhanced export was likely due to the decrease of the free volume inside the capsule. When the macromolecule was encapsulated along with the same bacteria in alginate beads (of similar sizes), bacterial growth led to about 1.5-fold (LB medium) increase in the export of the macromolecule (FIG. 7D) in comparison to the basal level (export of the contents with no cell growth inside capsule), while about 2.6-fold (LB medium) increase was obtained in the case of chitosan capsules.

Example 2

Enhancement of Circuit Stability by Microencapsulation and Compartmentalization

Figures 3A, 3B:
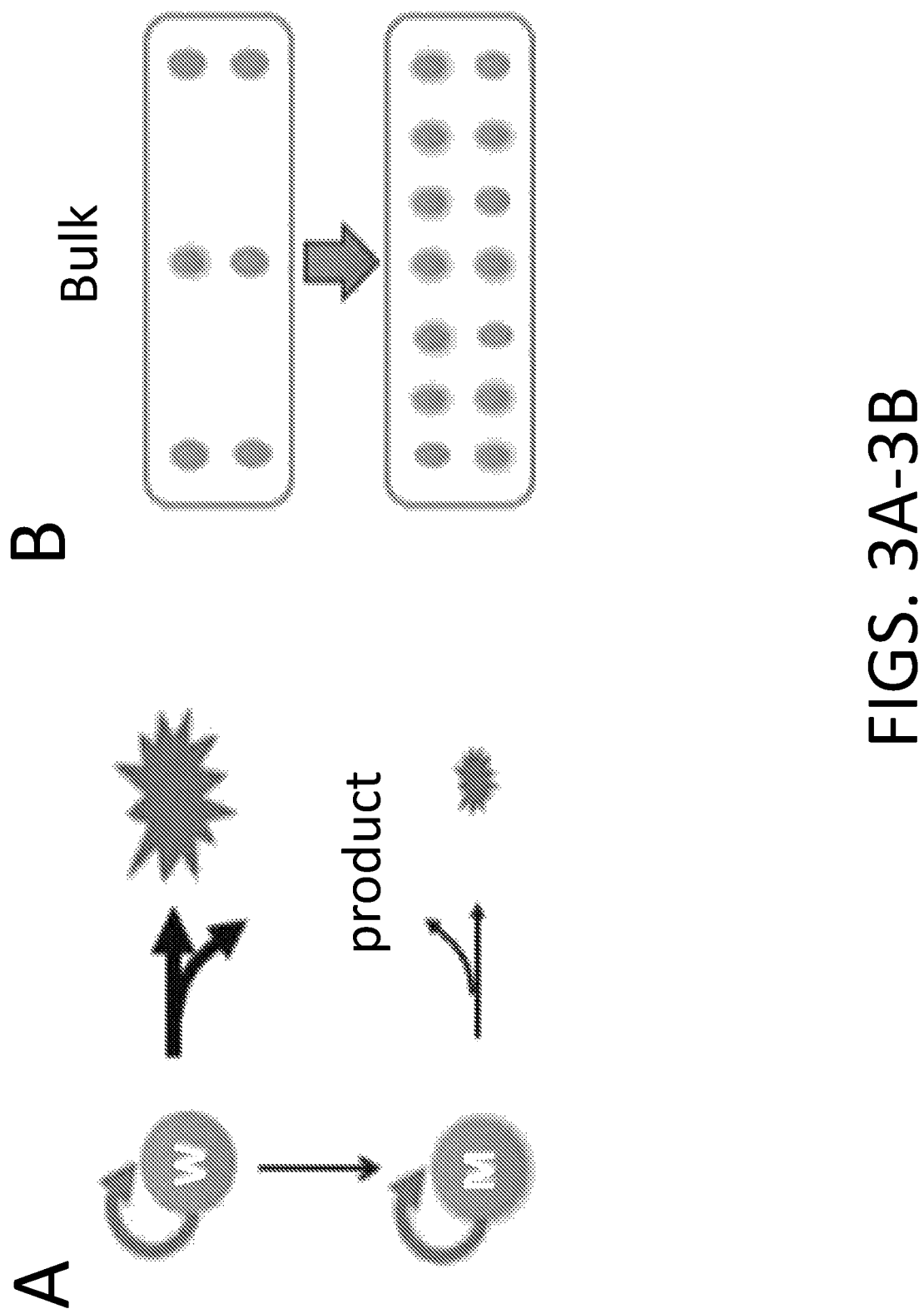
FIGS. 3A-3F include representative results demonstrating microencapsulation-mediated enhancement of circuit stability.
Figures 3C, 3D:
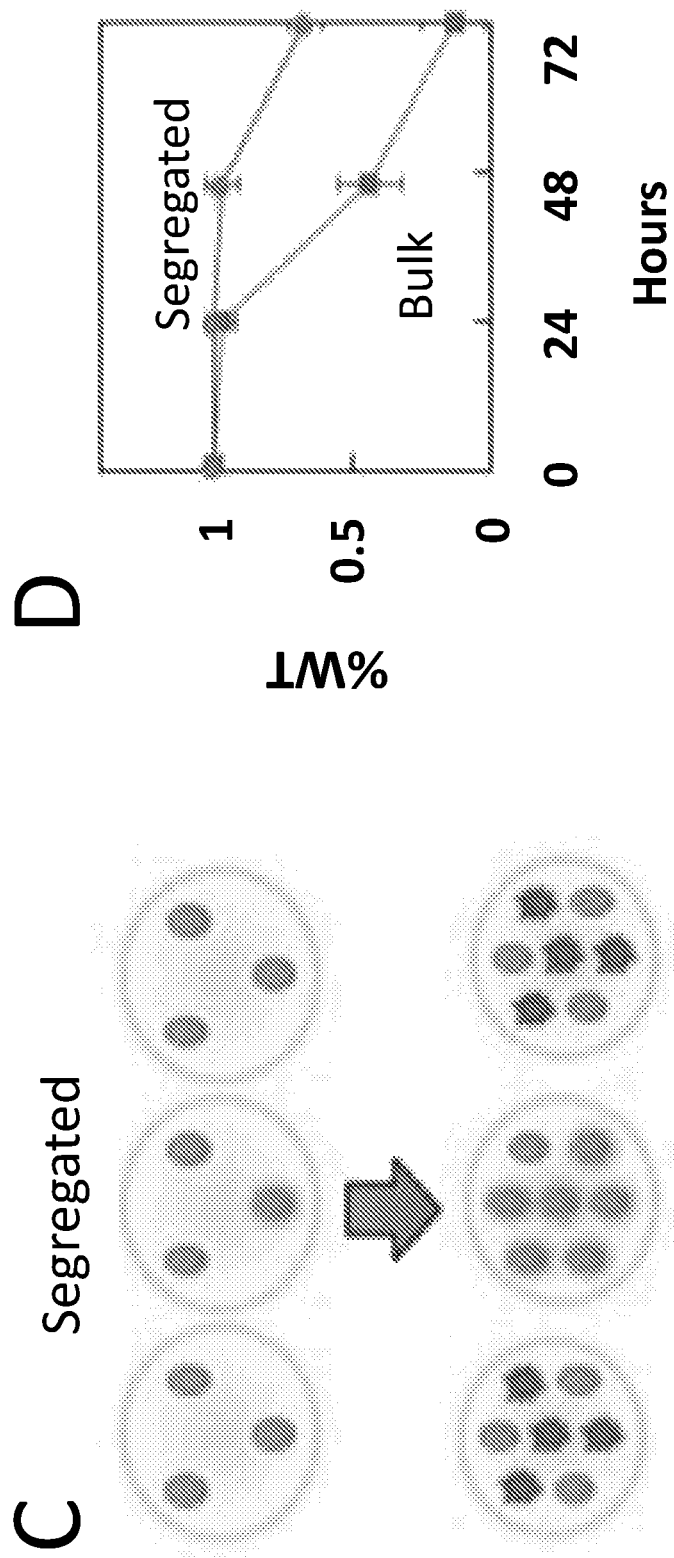
Figure 3E:
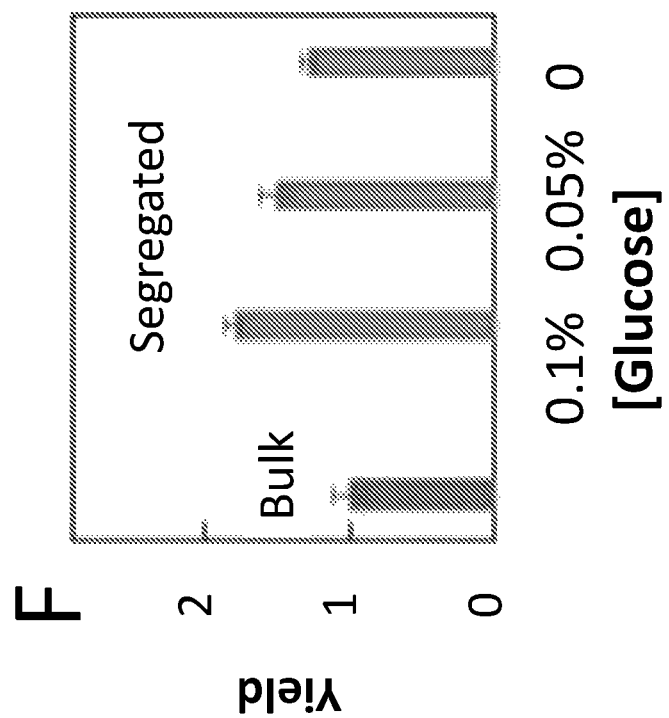
Figure 3F:
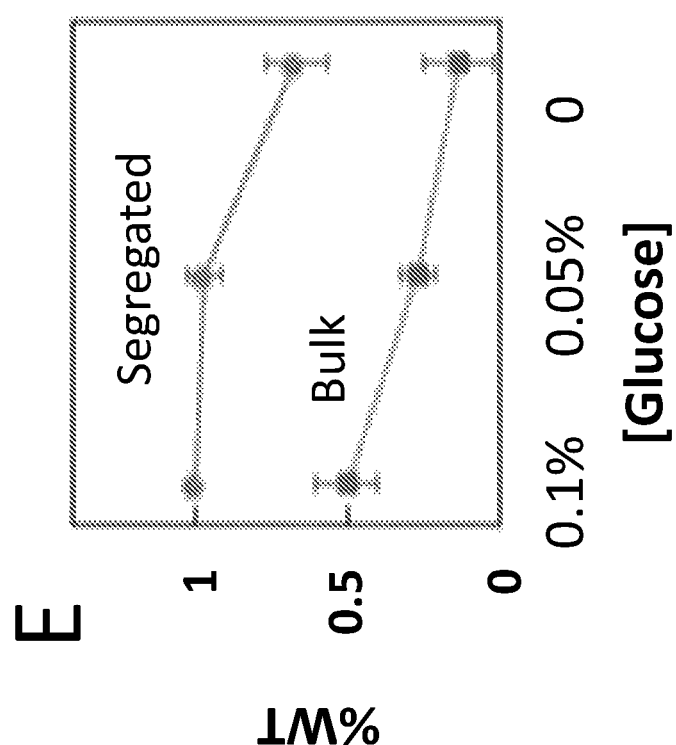

The density-dependent lysis programmed by ePop circuit is a functional aspect of the systems disclosed herein, as it functionally couples protein production and release. Yet, the programmed lysis creates a selection pressure for mutants that can escape killing (FIG. 3A). When this occurs, the mutant can take over the population, leading to loss of circuit function and reduced efficiency in autonomous protein release (FIG. 3B). By design, however, the system can enhance the genetic stability of the engineered circuit (FIG. 3C). First, the small population size in each microcapsule reduced the probability by which mutants can emerge in each microcapsule. This design concept was previously demonstrated in microfluidic analysis of a population controller, which has the same logic as the ePop circuit. Second, when a mutant emerges, it is confined within a capsule and will not contaminate the other encapsulated populations. Indeed, modeling analysis (FIGS. 8A, 8C, and 8D) and experimental results (FIGS. 3D-3F and FIG. 8B) provided herein demonstrate that combining these two factors significantly delayed takeover by a mutant and improved protein yield.

Example 3

Streamlined Enzymatic Quantification Using the MSB Platform on Chip

Figures 4A, 4B:
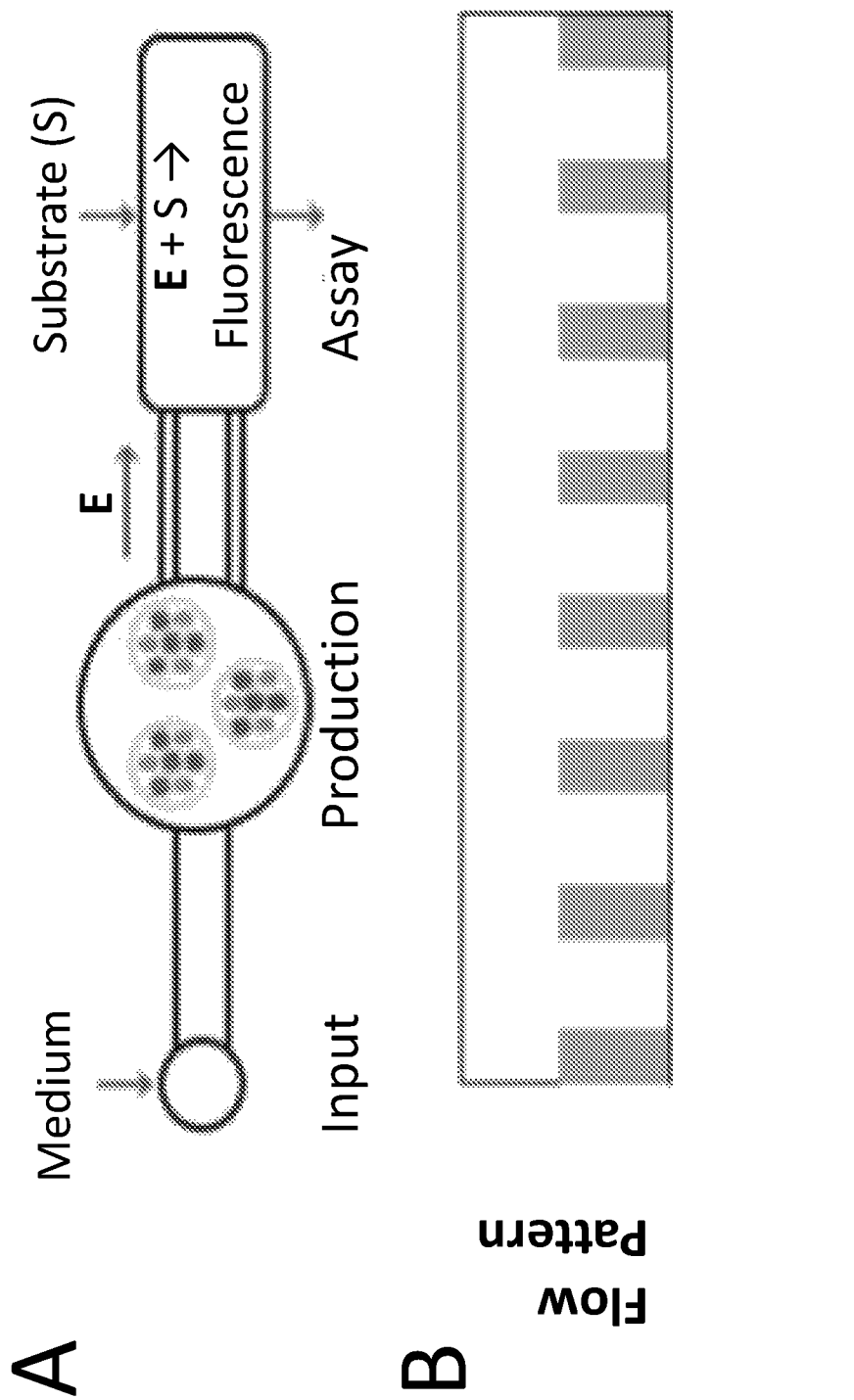
FIGS. 4A-4D include representative results demonstrating the sustained synthesis and quantification of BlaM.
Figures 9A, 9B:
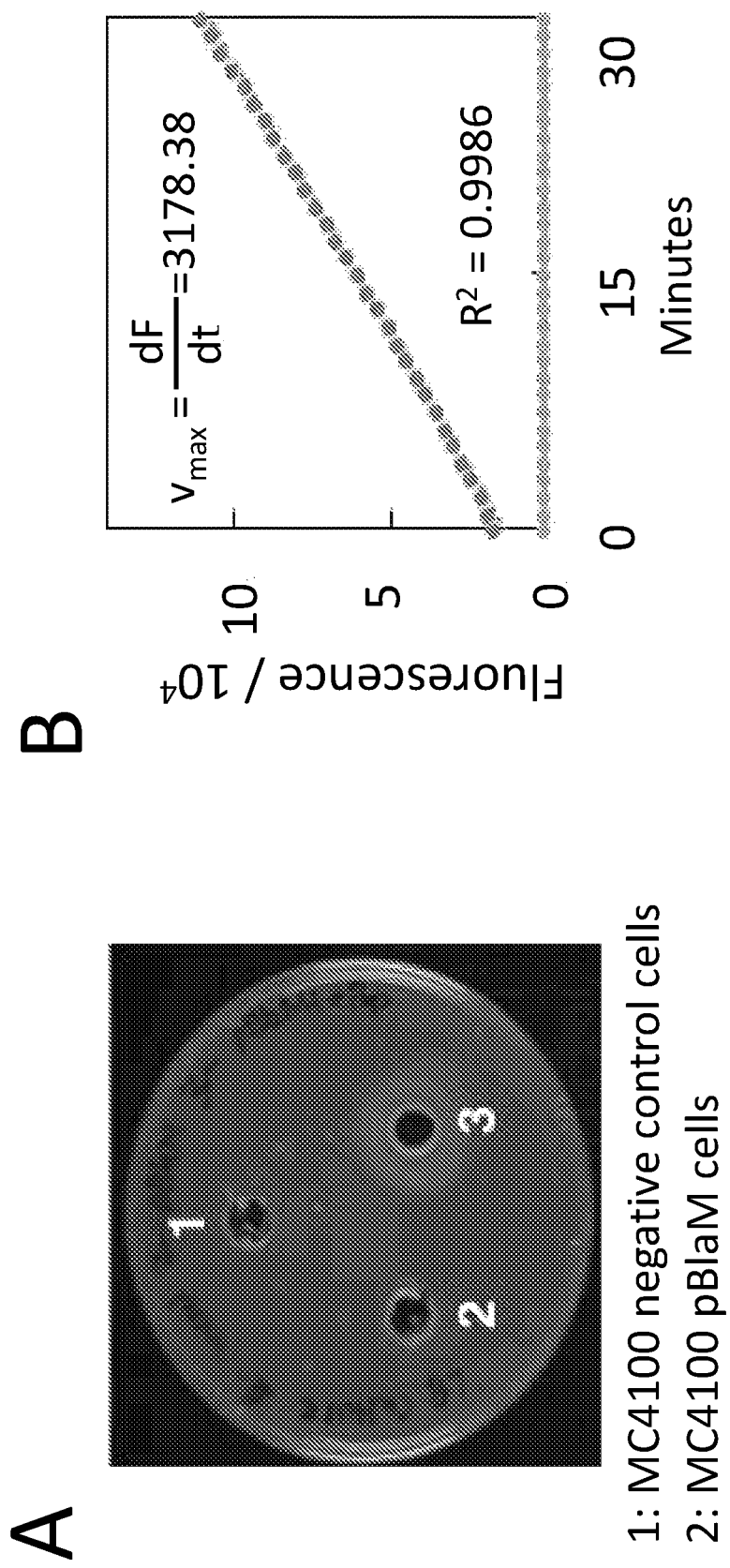
FIGS. 9A-9B include representative results demonstrating BlaM production as an exemplary protein for platform functional testing.

To demonstrate integrated protein synthesis and analysis, beta-lactamase was used as an exemplary protein. Briefly, the ePop bacteria was transformed with a plasmid encoding a modified beta-lactamase (BlaM) gene under an inducible promoter (MC4100Z1(ePop/BlaM)). In comparison with the wild type Bla, BlaM does not contain the periplasm-localization sequence. As a result, it is cytoplasmic and is functional only when the producing cell is lysed (FIG. 9A). This property allows for the evaluation of the MSB platform. To facilitate the control and analysis of the system dynamics, a microfluidic device was fabricated and included a production chamber and an assay chamber. The production chamber is fluidly coupled to an input channel, which allows loading of MSBs and flow-in of fresh medium. The output from the culture chamber is fluidly coupled to the assay chamber (FIG. 4A). A second channel was created in the assay chamber to supply fluorocillin, which can be converted by BlaM into a fluorescent product (FIG. 9B). This reaction provides a fast, quantitative readout for measuring BlaM activity.

Figures 4C, 4D:
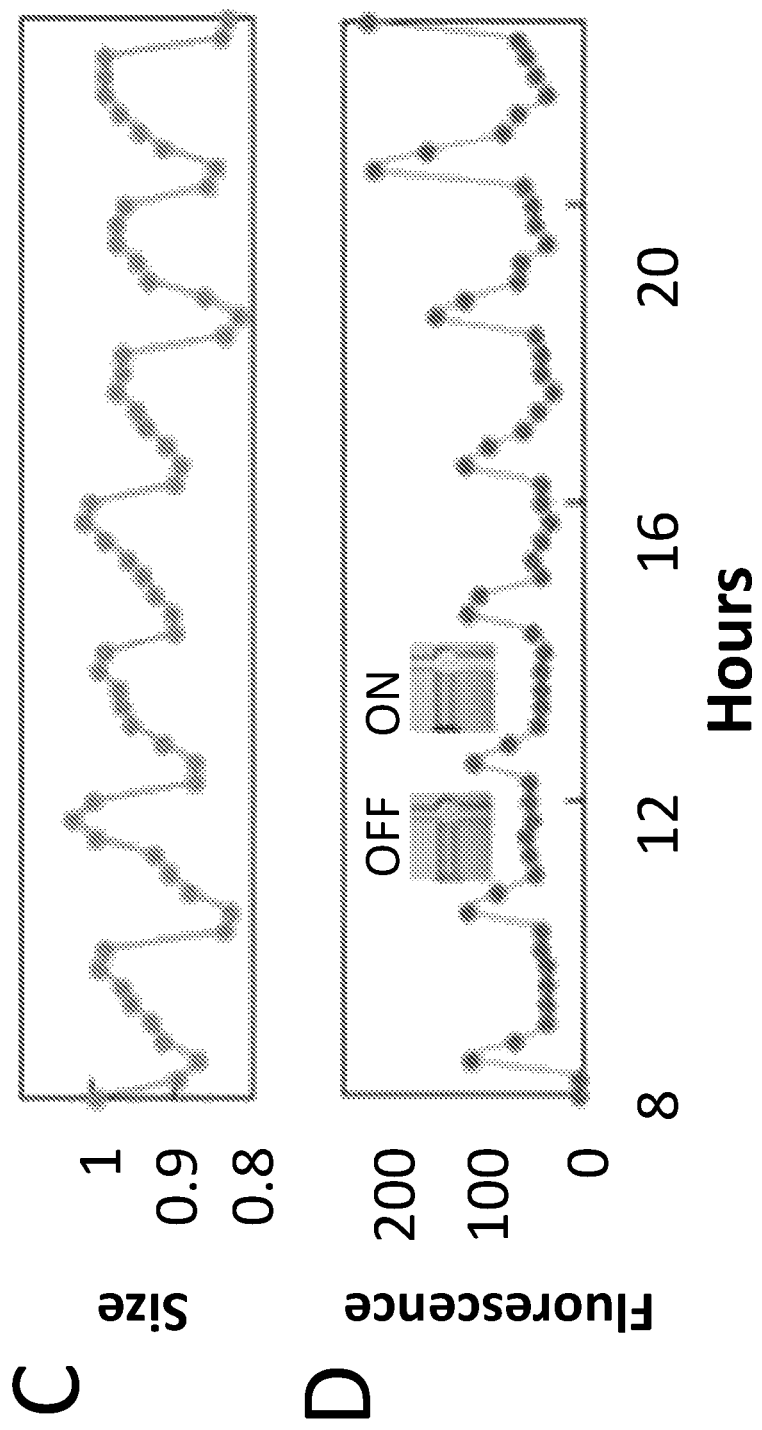

Fresh medium was periodically added (FIG. 4B), which led to synchronized oscillations of the capsule size in the culture chamber and periodic accumulation of fluorescence with the same periodicity in the assay chamber (FIG. 4C-4D). These results demonstrated the integrated synthesis and release of BlaM in a continuous manner due to our engineered MSB function. The multiple cycles of swollen to shrunk transition also demonstrate the robustness of MSB.

Example 4

Integration of the MSB Platform with Diverse Purification Modalities

The culture chamber containing MSBs can be integrated with a purification module without compromising continuity of operation. As an illustration, another exemplary protein was used, ELPs-GFP-His, which includes a His-tag and an elastin-like polypeptides (ELPs) tag (BL21(DE3) (ePop/ELPs-GFP-His)). His-tag allows purification by immobilized metal affinity chromatography (IMAC). ELPs are repetitive artificial polypeptides that undergo lower critical solution temperature phase transition behavior (FIG. 10A) in response to changes in temperature and salt concentrations, which can be exploited for protein purification as an orthogonal approach to IMAC.

Figure 5A:
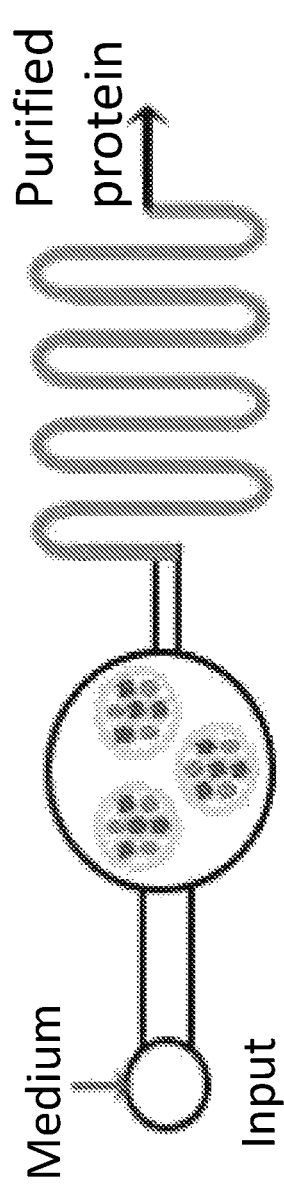
FIGS. 5A-5H include representative results demonstrating integrated protein production and purification.
Figure 5B:
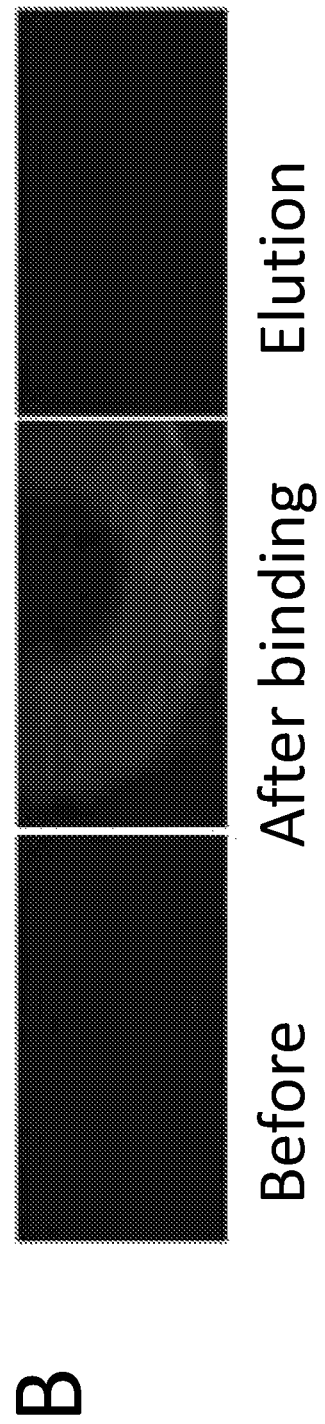

To demonstrate an online affinity-based purification, a purification chip was fabricated containing a serpentine channel. In this chip, the surface of the glass slide is modified with PEG-coated chelated $Cu^{2+}$. As the extruded lysate is transported from the production chamber to the purification chip (FIG. 5A), a His-tagged protein can bind to the chelated $Cu^{2+}$ on the glass surface, while other proteins are repelled by the PEG brushes. The bound His-tagged protein can subsequently be eluted. The microscopy image of purification process (FIG. 5B) showed the binding and elution of ELPs-GFP-His, which was produced and released from the MSBs in the production chamber.

Figures 5C, 5D:
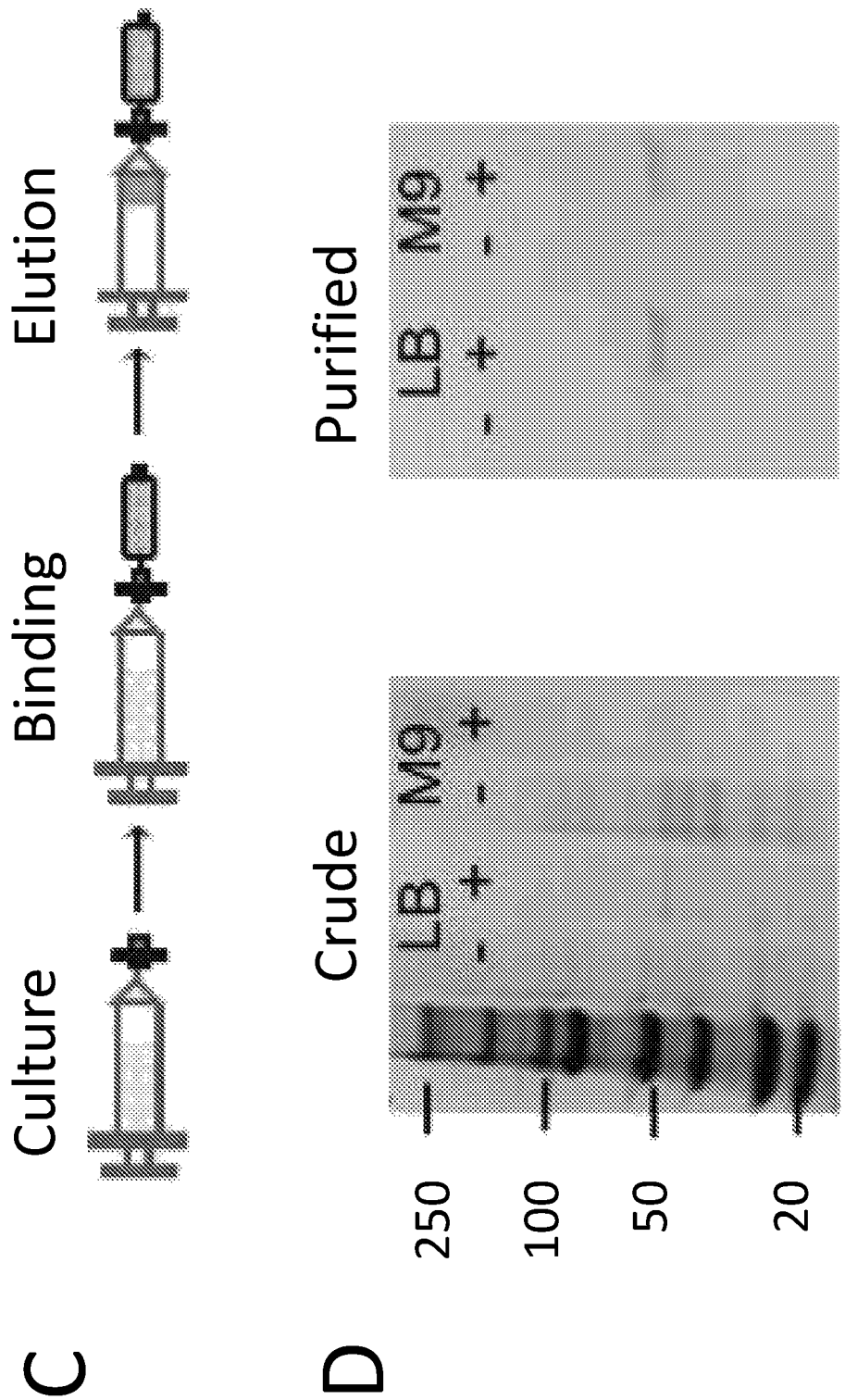

The MSB systems of the present disclosure are modular and scalable. On a larger scale, the protein production and release can be carried out on the bench top using a syringe loaded with MSBs. In particular, a 10-mL syringe was used as the production chamber and a syringe filter was attached to it. About 10,000 MSBs (containing a total of about $10^7$ bacteria) were loaded in the syringe and incubated in LB medium at 37° C. for 24 hours. The syringe was then connected, together with the syringe filter, to a Ni-NTA column (FIG. 5C). The bacterial lysate was pushed through the column, allowing the binding of His-tagged proteins. The MSBs were blocked by the syringe filter. After washing, the His-tagged proteins were eluted and analyzed by SDS-PAGE. FIG. 5D shows the successful purification of ELPs-GFP-His using this platform. For 24-hour production, a total production of 299 μg POI (protein-of-interest) was obtained using a 10 mL culture in LB medium in a single dose (yield was about 30 mg/L). Further details are provided below in Table 6.

TABLE 6

Production of ELPs/RLPs as single-dose (top two rows) or multi-dose (bottom two rows).

|  | ELPs-GFP-His | RLPs-GFP-His |
|---|---|---|
| Yield (mg/L) | 29.9 ± 3.4 | 36.9 ± 7.3 |
|  | 3 mL × 1 | 1.5 mL × 2 |
| Yield (mg/L) | 34.9 ± 2.9 | 40.6 ± 3.3 |

Protein production of ELPs-GFP-His and RLPs-GFP-His in the single-dose production using a syringe in 24 hours. The total culture volume was 10 mL LB medium. The yield was calculated by the total production divided by the total nutrients. Experiments were done in triplicate.

Figures 5E, 5F:
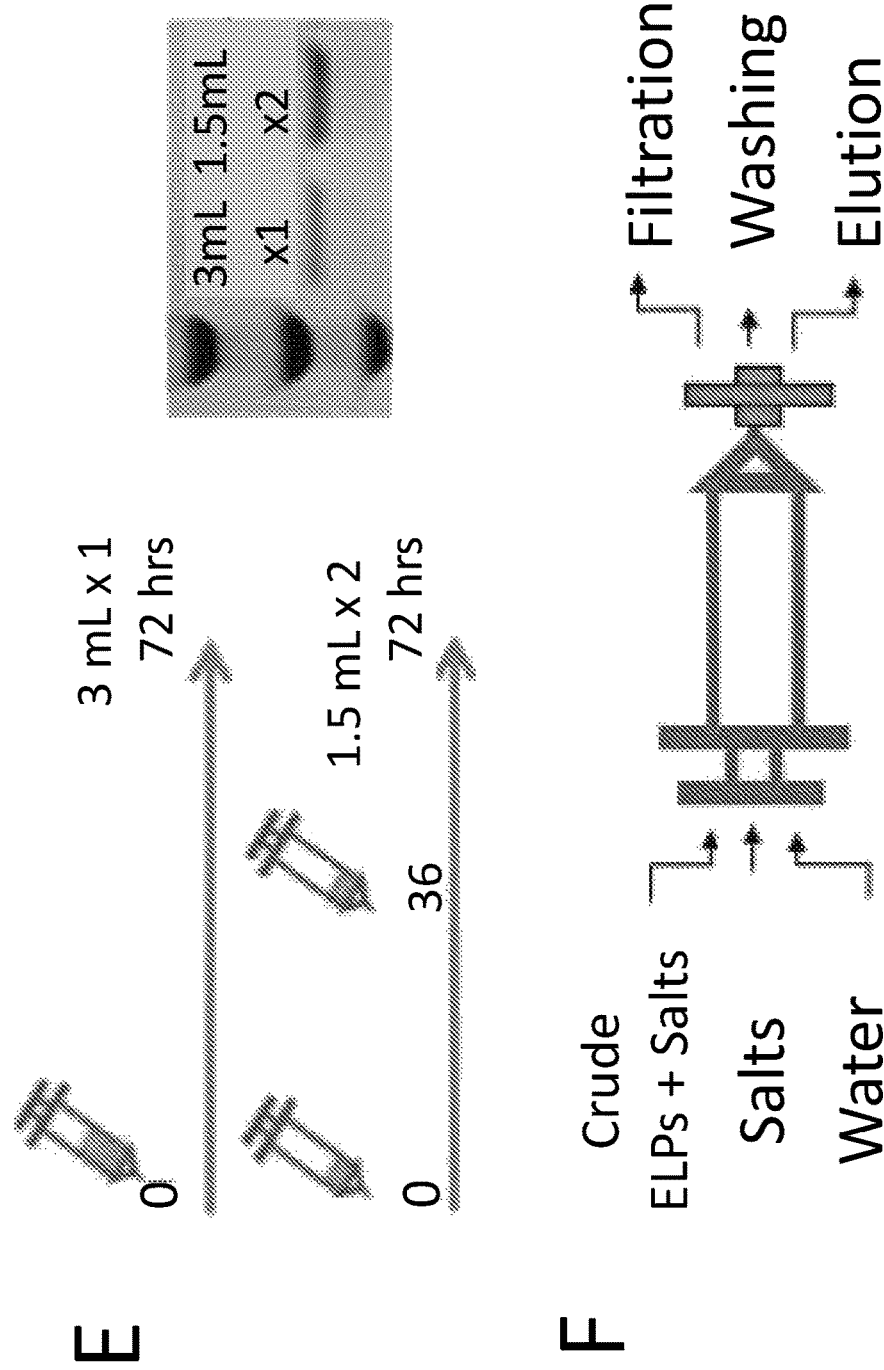

Protein production of ELPs-GFP-His by different dosing frequency with the same total nutrients. The total nutrients included 3 mL LB medium. The nutrients are dispensed in a periodic dosing way. For the sample 3 mL×1, 3 mL LB medium was supplemented at time 0 and collected on 72 hours. For the sample 1.5 mL×2, 1.5 mL LB medium was supplemented at time 0 and collected on 36 hours; and another 1.5 mL was supplemented at time 36 and collected on 72 hours. Experiments were done in triplicate The yield was further improved when the same amount of LB medium was supplied in multiple batches (FIG. 5E and Table 6). This improved yield was likely due to an increased export through multiple cycles of swelling and collapse, by the chitosan capsules and through multiple cycles of bacterial growth and lysis.

Figures 5G, 5H:
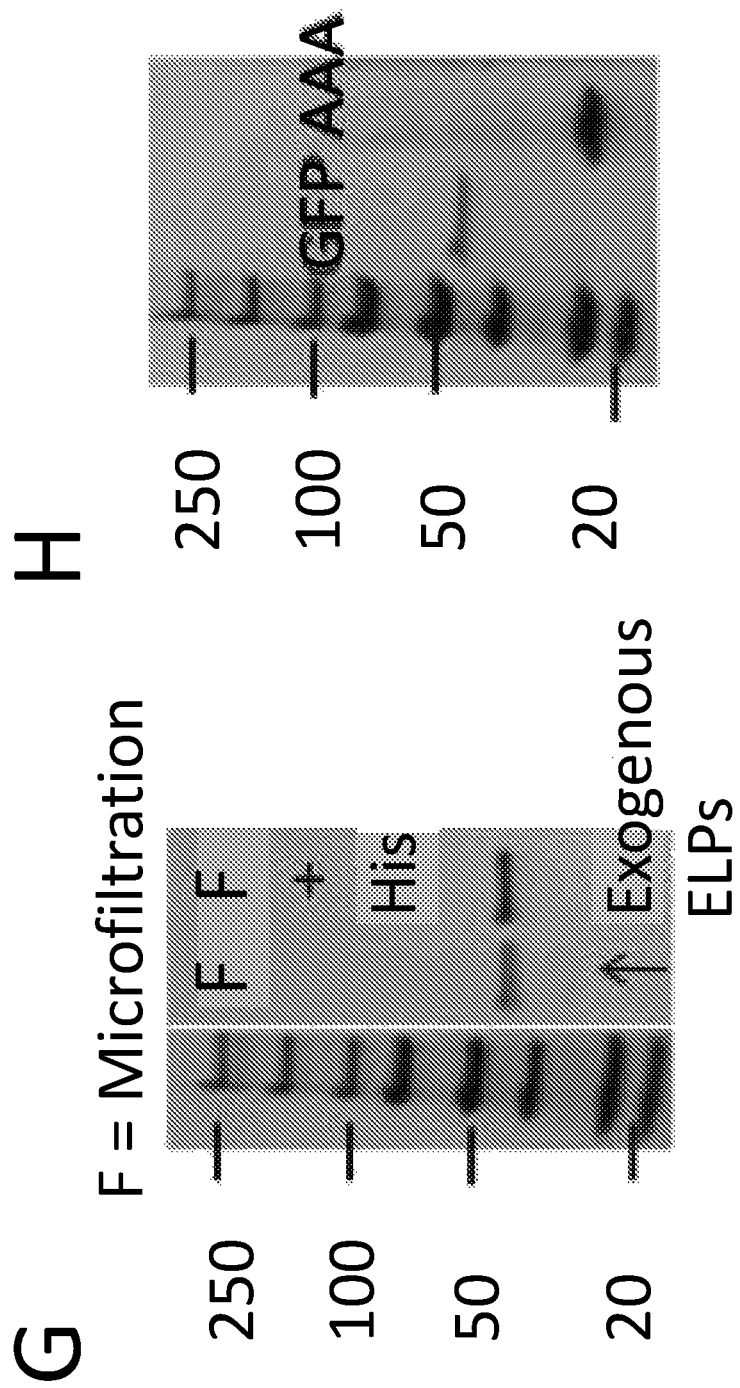
Figures 10A, 10B:
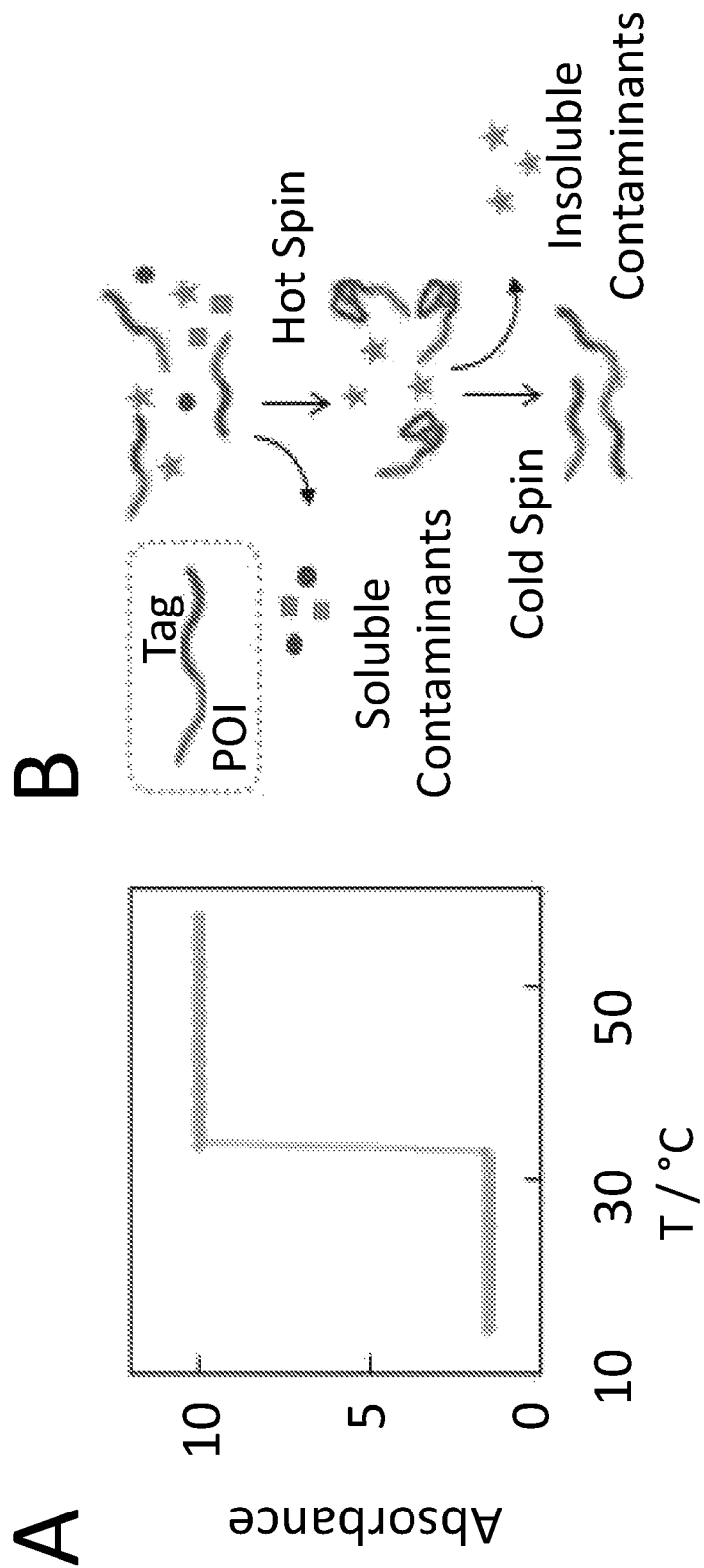
FIGS. 10A-10C include representative results demonstrating that elastin like polypeptides (ELPs) can function as thermal tags for purification due to their thermal sensitivity.
Figure 10C:

ELPs and ELPs-tagged proteins can undergo LCST phase transition in an aqueous solution, leading to formation of micron-sized aggregates. This property is often exploited for protein purification by using inverse transition cycling, which involves multiple cycles of temperature shift and centrifugation (FIG. 10B). To adapt the procedure into the system for a continuous and convenient operation, the LCST phase transition of ELPs were isothermally triggered at room temperature by adding salts and exogenous ELPs (FIG. 10C). The aggregates of ELPs or ELPs-tagged proteins were retained by a microfiltration membrane while the other constituents in the solution were washed away using a high-salt buffer at room temperature (FIG. 5F). The ELPs and ELPs-tagged proteins were then eluted using water. Indeed, the SDS-PAGE gel indicates the presence of both ELPs-GFP-His and exogenous ELPs in the elution fraction of microfiltration. After affinity purification by IMAC, only ELPs-GFP-His was evident on the protein gel, while the exogenously added ELPs was removed (FIG. 5G).

Combining the LCST phase behavior of ELPs-tagged protein with affinity His-tag provides two orthogonal methods, but highly complementary for protein purification, which enables the isolation of proteins with higher purity than is possible by either method alone. Moreover, these methods enable separation and purification of multiple proteins from the same crude, increasing the throughput of the purification. To demonstrate, the crude from two MSB cultures containing ELPs-GFP-His and another His-tagged protein (His-AAA, in which A represents a SpyTag peptide) were mixed. The use of His-tag purification alone did not separate them. However, by first going through a round of ELPs-based purification (induced aggregation+microfiltration), ELPs-GFP-His (as aggregates) was retained in the membrane while the His-AAA was in the solution. The two proteins were then separately purified by IMAC (FIG. 5H).

The MSB biomolecule production platform of the present disclosure enables the production and analysis or separation of any protein that can be expressed at a sufficiently high level. The results provided herein have demonstrated the production of a wide range of proteins, including multiple ELPs (some of them are fused with spytag and spycatcher), RLPs, ligand-binding protein, pigment protein and enzyme (FIGS. 11A-11E and Table 3).

Figures 11A, 11B, 11C:
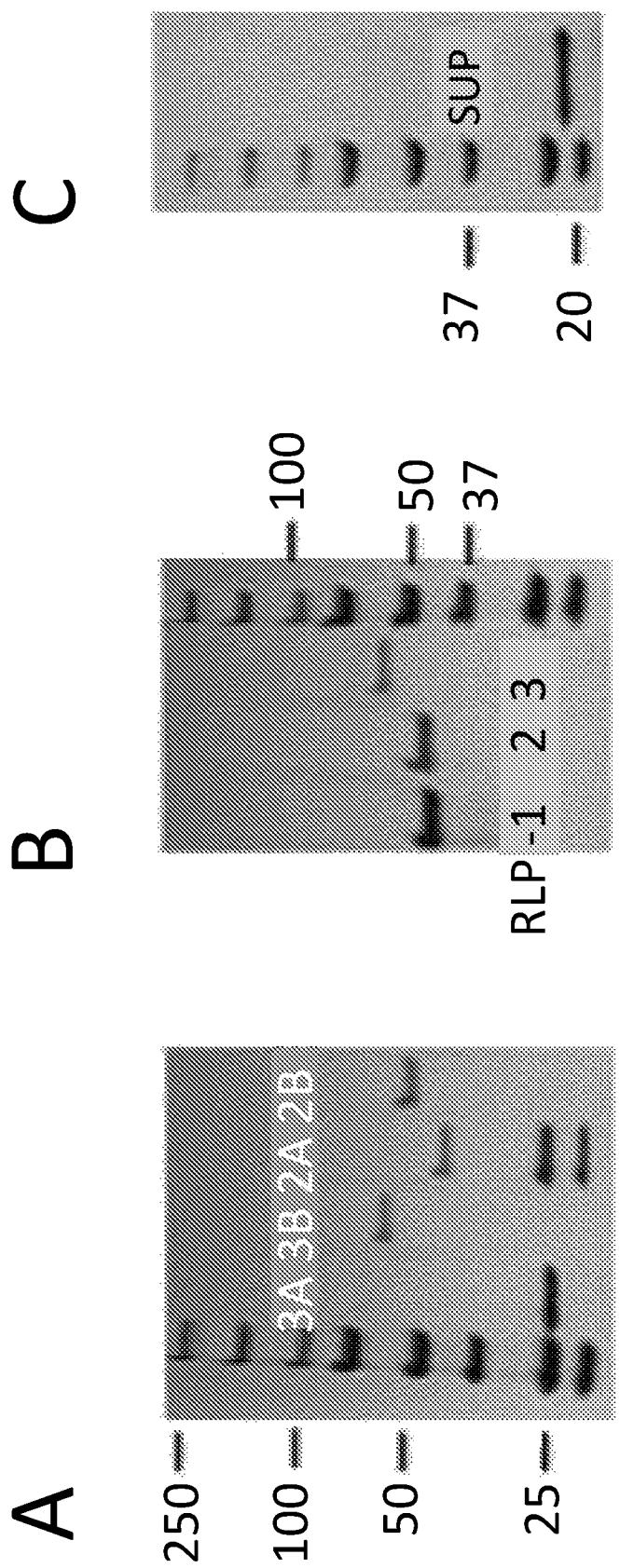
FIGS. 11A-11F include representative results demonstrating a wide range of proteins are expressed and purified in the MSB platform.
Figures 11D, 11E, 11F:
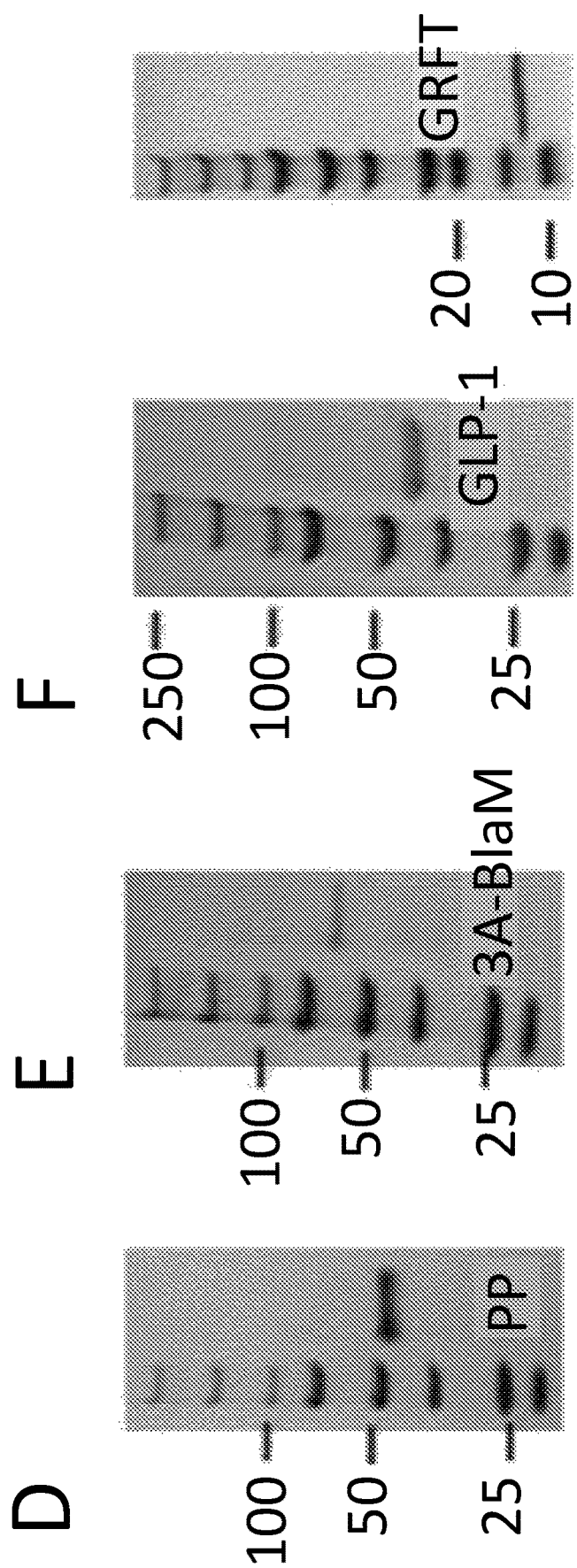
Figure 12A:
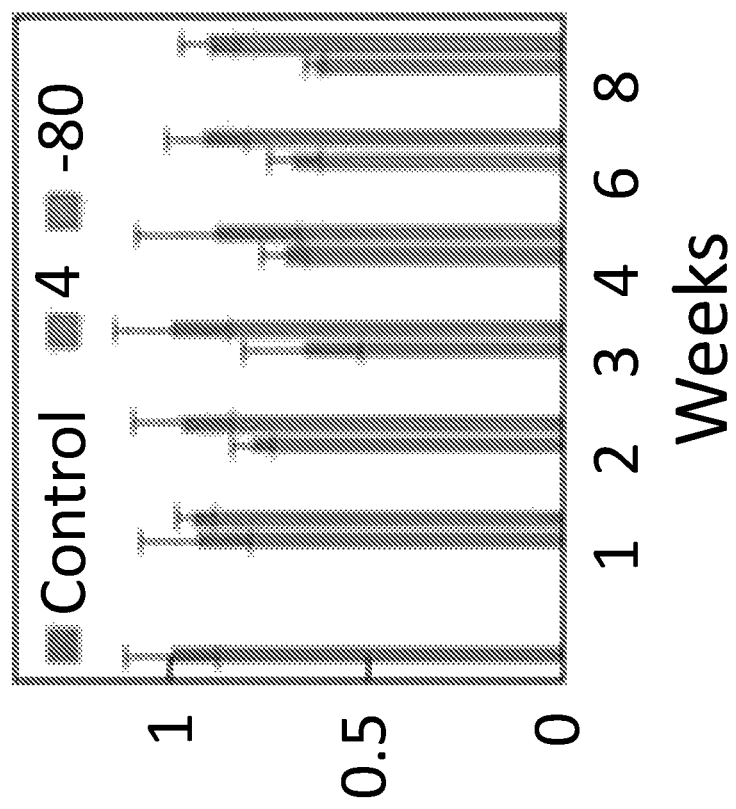
FIGS. 12A-12B include representative results demonstrating that the MSB platform is versatile, flexible and convenient and comprises simple components and operating procedures.
Figure 12B:
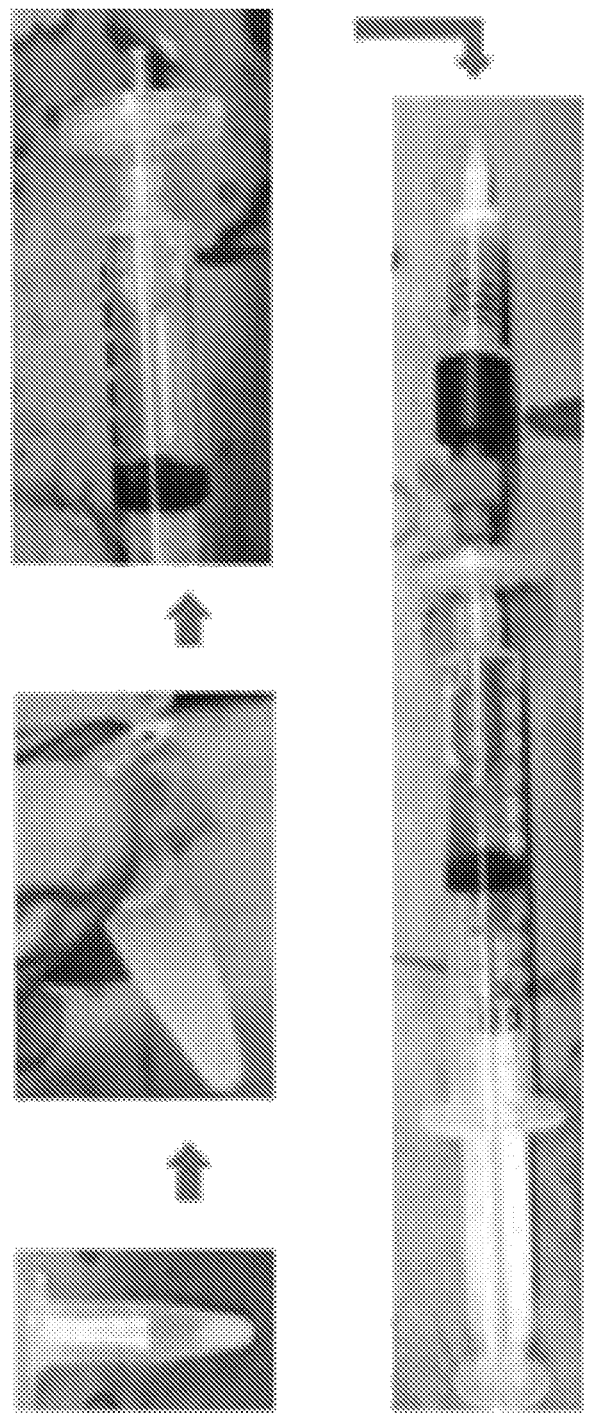

Also, this approach was extended to express multiple therapeutic biologics, including glucagon-like peptide 1 (GLP-1), that is used to treat type-2 diabetes, and griffithsin, a potent inhibitor of HIV and Zika infections (FIG. 11F). This capability can be extended to other biologics of interest, such as antimicrobial peptides and glycoprotein vaccine. The MSB biomolecule production platform also enables integrated screening or characterization of a biomolecule-of-interest, such as a protein (e.g., FIG. 4), or multiple and orthogonal modes of purification (FIG. 5). MSBs can be prepared in advance and kept at −80° C. for two months with negligible decrease in performance before dispatch (FIG. 12A). The operation is simple and straightforward and does not require large or expensive equipment or advanced expertise (FIG. 12B). Regardless of how the MSBs are fabricated, the biomolecule production platforms of the present disclosure use off-the-shelf accessories that are easy to set up. The purified protein can be produced with limited or no access to centrifuge, sonicator or electricity (Table 7). The operation is simple and can be conducted after minimal training. These properties are highly advantageous for a number of application contexts, such as personalized drug synthesis and accessible biomanufacturing in remote areas, including battlegrounds.

TABLE 7

Comparison between a conventional method and the MSB technology in terms of equipment required for protein synthesis, separation, and purification.

| Conventional Method | MSB Technology |
| --- | --- |
| Sonicator | |
| Centrifuge | |
| Flask/culture tube | Culture chamber |
| Syringe, filter, etc for purification | Syringe, filter |
| Affinity column | Affinity column |

It is understood that the foregoing detailed description and accompanying examples are merely illustrative and are not to be taken as limitations upon the scope of the disclosure, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the disclosure, may be made without departing from the spirit and scope thereof.

What is claimed is:

1. A system for biomolecule production, the system comprising:
   a plurality of genetically engineered microorganisms comprising a genetic circuit comprising a cell lysis module and a cell density sensing module, wherein the genetic circuit facilitates autonomous production of the biomolecule-of-interest; and
   an encapsulation material capable of forming microcapsules to contain the plurality of genetically engineered microorganisms, wherein the encapsulation material is responsive to one or more conditions in the microcapsules.

2. The system of claim 1, wherein the plurality of genetically engineered organisms comprise bacteria or yeast.

3. The system of claim 1, wherein the plurality of genetically engineered microorganisms comprise E. coli strains MC4100, MG1655, BL21, NISSLE1917, and any derivatives or variations thereof.

4. The system of claim 1, wherein the cell lysis module comprises a gene encoding E protein from phage phiX174, and wherein the cell density sensing module comprises a mutated luxR gene and a ColE1 origin of replication lacking the Rom/Rop protein.

5. The system of claim 1, wherein the biomolecule-of-interest is at least one of a peptide, a polypeptide, a protein, a nucleic acid, a polynucleic acid, a DNA molecule, a RNA molecule, or any derivatives or combinations thereof.

6. The system of claim 1, wherein the encapsulation material comprises chitosan, alginate, hyaluronic acid, polyethylene glycol polymers, polyethylene oxide polymers, elastin-like polypeptides (ELPs), resilin-like polypeptides (RLPs), or any derivatives or combinations thereof.

7. The system of claim 1, wherein the cell lysis module and the cell density sensing module are configured to control copy number of a plasmid comprising or encoding the biomolecule-of-interest.

8. The system of claim 1, wherein the plurality of genetically engineered microorganisms alters the one or more conditions in the microcapsules.

9. The system of claim 8, wherein the one or more conditions in the microcapsules comprise pH or ionic strength.

10. A microfluidics platform for biomolecule production, the platform comprising:
  a microfluidic device comprising an input channel, a production chamber, and an assay chamber,
  a plurality of genetically engineered microorganisms comprising a genetic circuit comprising a cell lysis module and a cell density sensing module, wherein the genetic circuit facilitates autonomous production of a biomolecule-of-interest; and
  an encapsulation material capable of forming microcapsules to contain the plurality of genetically engineered microorganisms, wherein the encapsulation material is responsive to one or more conditions in the microcapsules.

11. The microfluidics platform of claim 10, wherein the production chamber is fluidly coupled to the input channel and the assay chamber.

12. The microfluidics platform of claim 10, wherein the plurality of genetically engineered microorganisms are contained in the production chamber.

13. The microfluidics platform of claim 10, further comprising an output channel fluidly coupled to the assay chamber or the production chamber.

14. The microfluidics platform of claim 10, further comprising a second input channel fluidly coupled to the assay chamber.

15. The microfluidics platform of claim 10, wherein the production chamber is fluidly coupled to a purification chip.

16. The microfluidics platform of claim 15, wherein the inner surface of the purification chip is modified to bind the biomolecule-of-interest.

17. A method for producing a biomolecule-of-interest, the method comprising:
  loading a plurality of genetically engineered microorganisms contained in microcapsules into a microfluidics device, wherein the plurality of genetically engineered microorganisms comprise a genetic circuit comprising a cell lysis module and a cell density sensing module, and wherein the microcapsules are formed from an encapsulation material that is responsive to one or more conditions in the microcapsules;
  providing nutrients to the plurality of microorganisms; and
  producing the biomolecule-of-interest.

18. The method of claim 17, wherein the encapsulation material comprises chitosan, alginate, or any derivatives or combinations thereof.

19. The method of claim 17, wherein the microfluidics device comprises an input channel, a production chamber, and an assay chamber.

* * * * *